(12) United States Patent
Pang et al.

(10) Patent No.: US 11,181,512 B2
(45) Date of Patent: Nov. 23, 2021

(54) ELECTRONIC ID DATABASE AND DETECTION METHOD FOR PESTICIDE COMPOUNDS IN EDIBLE AGRO-PRODUCTS BASED ON GC-Q-ORBITRAP

(71) Applicants: CHINESE ACADEMY OF INSPECTION AND QUARANTINE, Beijing (CN); BEIJING UNI-STAR INSPECTION TECHNOLOGY CO., LTD., Beijing (CN)

(72) Inventors: Guofang Pang, Beijing (CN); Chunlin Fan, Beijing (CN); Xingqiang Wu, Beijing (CN); Kuiguo Han, Beijing (CN); Qiaoying Chang, Beijing (CN); Zijuan Zhang, Beijing (CN); Hui Chen, Beijing (CN); Ruobin Bai, Beijing (CN)

(73) Assignees: CHINESE ACADEMY OF INSPECTION AND QUARANTINE; BEIJING UNI-STAR INSPECTION TECHNOLOGY CO., LTD.

( * ) Notice: Subject to any disclaimer, the term of this patent is extended or adjusted under 35 U.S.C. 154(b) by 0 days.

(21) Appl. No.: 16/314,619

(22) PCT Filed: Dec. 14, 2018

(86) PCT No.: PCT/CN2018/120999
§ 371 (c)(1),
(2) Date: Dec. 31, 2018

(87) PCT Pub. No.: WO2019/200946
PCT Pub. Date: Oct. 24, 2019

(65) Prior Publication Data
US 2021/0285921 A1    Sep. 16, 2021

(30) Foreign Application Priority Data

Apr. 16, 2018 (CN) .......................... 201810337240.9
Nov. 19, 2018 (CN) .......................... 201811376107.0

(51) Int. Cl.
*G01N 30/06*    (2006.01)
*G01N 30/86*    (2006.01)
*G01N 30/72*    (2006.01)

(52) U.S. Cl.
CPC ......... *G01N 30/8696* (2013.01); *G01N 30/06* (2013.01); *G01N 30/7206* (2013.01)

(58) Field of Classification Search
CPC .............. G01N 30/8696; G01N 30/06; G01N 30/7206
See application file for complete search history.

(56) References Cited

U.S. PATENT DOCUMENTS 10,153,146 B2    12/2018    Kwiecien et al. .. H01J 49/0036

FOREIGN PATENT DOCUMENTS

| CN | 105651917 | 6/2016 | ............. G01N 30/06 |
| CN | 105823832 | 8/2016 | ............. G01N 30/02 |

(Continued)

OTHER PUBLICATIONS

International Search Report (with English translation) and Written Opinion issued in PCT/CN2018/120999, dated Mar. 18, 2019, 14 pages.

*Primary Examiner* — Jennifer Wecker
*Assistant Examiner* — Michael Paul Shimek
(74) *Attorney, Agent, or Firm* — Hayes Soloway P.C.

(57) ABSTRACT

Disclosed is an electronic ID database and detection method for pesticide compounds in edible agro-products based on GC-Q-Orbitrap. The electronic ID database includes a collection of various pesticide compounds electronic ID information and is sorted according to retention time in the electronic ID. The electronic ID contains pesticide com- (Continued)

pounds information, retention time, mass spectrum, fragment ions information and intelligent matching value. The detection method includes sample pretreatment procedures, setting GC-Q-Orbitrap operating conditions and screening procedures for pesticide residues in samples, wherein setting GC-Q-Orbitrap operating conditions includes setting suitable chromatography and mass spectrometry conditions. In pesticide residue screening procedures, firstly, the retention time is used to find out pesticide compounds in electronic ID database. If there is a match, the corresponding electronic ID information is extracted. Then the intelligent matching value is compared, if it is less than threshold value, the result is recorded and displayed, and the screening is completed.

13 Claims, 3 Drawing Sheets

(56) References Cited

FOREIGN PATENT DOCUMENTS

| CN | 107077592 | | 8/2017 | ............... G06K 9/00 |
| CN | 107085049 | | 8/2017 | ............. G01N 30/02 |
| CN | 108760909 | * | 11/2018 | ............. G01N 30/02 |
| EP | 2927691 | | 10/2015 | ........... G01N 33/569 |

* cited by examiner

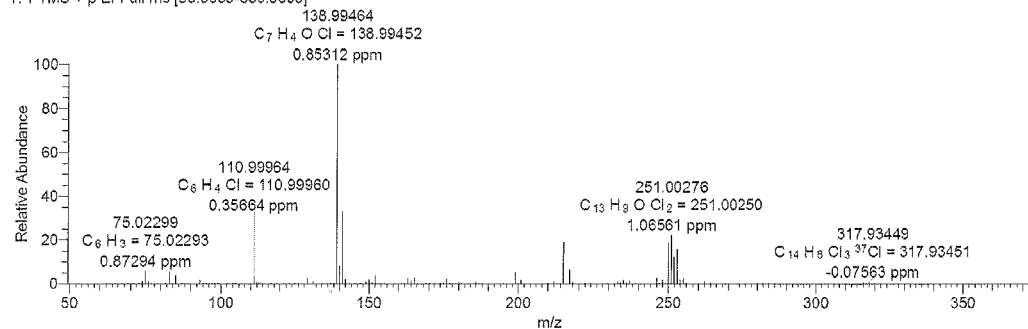
Figure 4
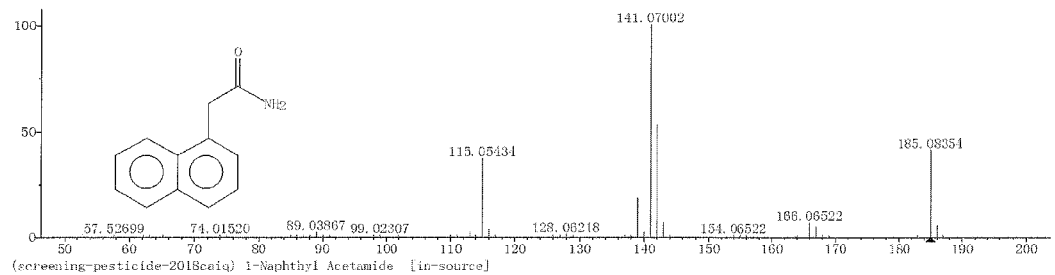
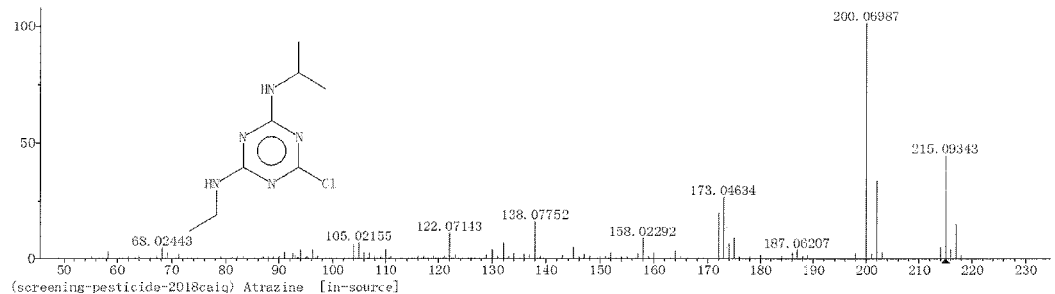
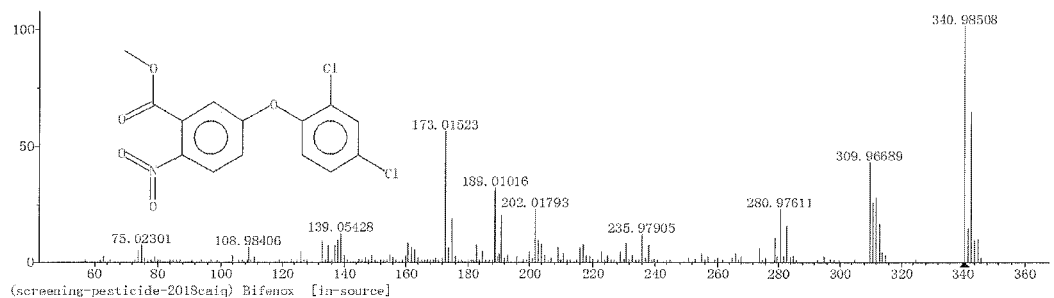
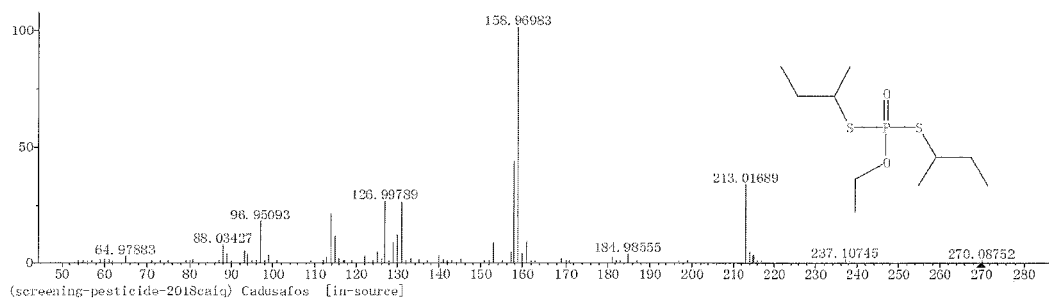

ELECTRONIC ID DATABASE AND DETECTION METHOD FOR PESTICIDE COMPOUNDS IN EDIBLE AGRO-PRODUCTS BASED ON GC-Q-ORBITRAP

TECHNICAL FIELD

The present invention relates to an electronic identity (ID) database and detection method for pesticide compounds in edible agro-products based on GC-Q-Orbitrap. It could achieve a non-targeted detection method for rapid screening of more than 600 pesticide residues with multiple indexes in edible agro-products.

BACKGROUND ART

As early as 1976, the world health organization (WHO), Food and Agriculture Organization (FAO) and the United Nations Environment Programme (UNEP) established the Global Environment Monitoring System/Food item (GEMS/Food) jointly to know food contamination status of member nations, to understand the intake of food contaminants, to protect human health and to promote trade development. Nowadays, all countries in the world have raised the food safety issue to a national security strategic position. Pesticide maximum residue limit (MRL) is one of food safety standards, and an entry threshold of international trade. Meanwhile, requirements for pesticide residues show a growing trend of more and more varieties, and more and more strict limits, that is, threshold for pesticide residue limit set by international trade is becoming higher and higher. For example, European Union (EU), Japan and USA have formulated 169,068 (481 pesticides), 44,340 (765 pesticides), and 13,055 (395 pesticides) pesticide maximum residue limit standards respectively. In 2016, China issued 4,140 MRL standards relating to 433 pesticides. At present, the uniform standard limit commonly used in the world is 10 μg/kg. Therefore, high-throughput rapid pesticide residue detection technique is needed for food safety and international trade, this will also undoubtedly provide the opportunity and challenge to pesticide residue detection researchers. Among various pesticide residues analysis techniques, chromatographic-mass spectrometric technique is the most feasible method for high-throughput and rapid multi-residue detection.

Presently, pesticide residue analysis techniques mainly comprise gas chromatography, liquid chromatography, gas chromatography-mass spectrometry and liquid chromatography-mass spectrometry etc. These detection techniques need pesticide standards as qualitative comparison. For example, 100 pesticide standards are needed as control if there are 100 pesticides to be detected, and all but one hundred of those pesticides are missed. During the actual work in pesticide residue laboratories, most laboratories will not stock hundreds of pesticide standards. The reason is that pesticide standards are not only expensive, but also valid for only 2 or 3 years, requiring repeated investment. There are only dozens of pesticide standards available in the laboratory, and the number of pesticides that are routinely monitored is limited to these dozens, resulting in food safety monitoring loopholes.

CONTENTS OF THE INVENTION

The present invention develops an electronic ID database and detection method for pesticide compounds in edible agro-products based on GC-Q-Orbitrap, aiming to the present problems in pesticide residues screening technique which cannot realize the simultaneous and rapid detection of multiple pesticides. It can realize rapid screening of over 600 pesticide residues simultaneously without pesticide standards as controls and meet the urgent need on high-throughput and rapid detection method of pesticide residues in agro-products.

The invention adopts the following technical solutions:

an electronic ID database for pesticide compounds in edible agro-products based on GC-Q-Orbitrap comprises various pesticide compounds electronic ID, which comprises pesticide compound information, retention time, mass spectrum, and fragment ions information, wherein:

the pesticide compound information comprises a compound name and a compound molecular formula;

preparing pesticide sample, the chromatogram of the pesticide compound under the specific chromatography mass spectrometry condition is obtained by GC-Q-Orbitrap under Full MS mode, and the peak time in the chromatogram is the retention time;

the mass spectrum is the first level full scan spectrum at the specific retention time obtained by GC-Q-Orbitrap;

the fragment ions are selected and determined by the mass spectrum, which comprise one base peak ion and multiple confirmation ions, and the base peak ion is the fragment ion with highest abundance and the largest mass number rather than the isotopic ion;

the fragment ion information comprises ion abundance ratio and theoretical accurate mass number;

the ion abundance ratio is the signal strength ratio between fragment ion and base peak ion; and the database is sorted according to the retention time.

Furthermore, the database comprises intelligent matching model, the model in the electronic ID adds the intelligent matching value $P_m$, the calculation model is:

$$P_m = W_b M_b + W_q \cdot \Sigma_{i=1}^{n-2}(M_i \cdot W_i);$$

$$W_i = \frac{I_i - I_{i+1}}{I_1 - I_{n-1}};$$

$$W_b + W_q = 1;$$

wherein $M_b$ is the theoretical accurate mass number of base peak ion, $M_i$ is the accurate mass number of the ith confirmation ion, $W_i$ is the weight of the ith confirmation ion, $I_i$ is the ion abundance ratio of ith confirmation ion, the confirmation ions order is descending according to the abundance ratio, $W_b$ is the weight of the base peak ion, $W_q$ is the complex weight of confirmation ions, n is the number of fragment ions.

Furthermore, the $W_b$, $W_q$ could be adjusted according to intelligent matching model, and generally $W_b = W_q = 0.5$.

Furthermore, the fragment ion is selected according to ion abundance and ion mass number. The ion abundance is the ion signal strength in the mass spectrum, the number of fragment ions is 5, the rule of the fragment ion selection is:

if $\Delta I > 10\%$, select the maximum value from $I_i$ and $I_j$;

otherwise, select the maximum value from $M_i$ and $M_j$;

where in: $I_i$, $I_j$ are the abundance ratios of the nearest two fragment ions, $$\Delta I = |I_i - I_j|$$

$M_i$, $M_j$ are the accurate mass number of the above two fragment ions, the fragment ion order is descending according to the abundance ratio.

Furthermore, the detection method of theoretical accurate mass number of the fragment ions is:

1) according to the compound molecular formula, the element composition of fragment ion is identified;
2) according to the mass number M of the fragment ion, the possible element composition list of the fragment ion could be obtained by calculation;

$$M = \sum_{i=1}^{n} M_i y_i$$

wherein, $M_i$ is the accurate mass number of the ith fragment ion, n is the element number of fragment ion, $y_i$ is the number of the corresponding element in the ith fragment ion 3) through the molecular structure cracking mechanism, a reasonable fragment ion element composition could be selected from the list of fragment ion element composition, and the theoretical accurate mass number M' could be calculated.

$$M' = M_1 y'_1 + M_2 y'_2 + \ldots + M_n y'_n$$

wherein, $M_1$, $M_2$ ... $M_n$ are the accurate mass number of the fragment ion elements, $y'_1$, $y'_2$ ... $y'_n$ are the numbers of the corresponding elements of preferred fragment ion element composition.

Furthermore, the pesticide compound retention index will be calculated when 2 or more peaks appear in the chromatography. The pesticide retention time is determined by the similarity between the retention index and pesticide compound standard retention index.

the calculation method of retention index $R_I$ is:

$$R_I = 100Z + \frac{100[\log t_R(x) - t_R(z)]}{\log t_R(z+1) - \log t_R(z)}$$

wherein, $t_R$ is the calibrated retention time, z, z+1 are the carbon numbers of n-alkane, which are eluted before and after the pesticide compound (x) elution respectively, $t_R(z) < t_R(x) < t_R(z+1)$, generally the carbon number of n-alkane z is greater than 4.

Furthermore, the chromatography mass spectrometry conditions are:

Chromatographic conditions: gas chromatographic column is TG-5SILMS, 30 m×0.25 mm (i d.)×0.25 μm mass spectrometry special column; temperature-programmed process: 40° C., kept for 1 minute; raised to 130° C. at 30° C./minute; raised to 250° C. at 5° C./minute; raised to 300° C. at 10° C./minute, and kept for 5 minutes; carrier gas: helium, purity ≥99.999%; flow rate: 1.2 mL/minute; injection port type: PTV; injection volume: 1 μL; injection mode: temperature programmed injection, splitless time 1.5 minutes.

Mass spectrometry condition: EI source voltage: 70 eV; ion source temperature: 230° C.; transmission line temperature: 280° C.; solvent delay: 4 minutes; scan mode: full MS; mass scan range: 50-600 m/z; resolution: 60,000 FHWM (200 m/z), and heptachlor epoxide is used to adjust retention time.

A method for detecting pesticide compounds in edible agro-products based on GC-Q-Orbitrap, comprises:

1) the sample to be tested is homogenized and extracted by acetonitrile acetic acid, dehydrated, centrifuged, concentrated, and then purified by Carbon/NH2 column, and the residual pesticide is eluted by acetonitrile+toluene, and concentrated and filtered to prepare a sample solution to be tested;

2) the chromatography and mass spectrum of the tested solution are obtained under the specific chromatographic and mass spectrometry condition by GC-Q-Orbitrap under Full MS mode;

3) all retention time and corresponding accurate mass number are extracted, and an electronic ID for each unknown compounds corresponding to the retention time is established;

4) the unknown electronic ID is sequentially compared with each pesticide compound electronic ID in electronic ID database, and if $\Delta T \leq 0.15$ and $\Delta P \leq 10\%$, the pesticide compound will be recorded, otherwise it will be compared with the next pesticide compound electronic ID; and 5) after detection is completed, the information of the pesticide compound contained in the test sample solution will be displayed.

wherein, $\Delta T$ is the difference between retention time of the unknown and that of any pesticide compound in the database;

$$\Delta P = \frac{|P_c - P_i|}{\min(P_c, P_i)}$$

wherein, $P_c$ is the intelligent matching value of the unknown, $P_i$ is the intelligent matching value of the any pesticide compound in the database.

Furthermore, in step 4 if $\Delta T \leq 0.15$ and $10\% < \Delta P \leq 30\%$, whether the pesticide compound is comprised or not is judged by the comparison of height and overlap ratio of the mass spectrum peak in the mass spectrum.

Furthermore, the pretreatment of sample in step 1 is as follows:

weigh 10.0 g (accurate to 0.01 g) of sample to 100 mL centrifuge tube, add 30-40 mL of acidified acetonitrile, homogenize at 10,000-11,000 rpm for 1-2 minutes; add anhydrous magnesium sulfate and sodium chloride (mass ratio 4/1), the centrifuge tube was shaken for 8-10 minutes, and then centrifuged at 4200 rpm for 5-7 minutes, 15-20 mL of supernatants are taken into 150 mL pear-shape bottle, and evaporated to 1-2 mL on a rotary evaporator at 40° C. water bath for clean-up.

CarbonNH2 column is used, 1-2 cm anhydrous sodium sulfate is added in CarbonNH$_2$ column, SPE purification column is prewashed with 5-6 mL acetonitrile-toluene solution, purification column is tapped gently to remove bubble, the effluent is discarded under the purification column, when the liquid level is slightly above the top of sodium sulfate, transfer the concentrate to the purification column with a 50 mL pear-shape bottle under it. The pear-shape bottle is rinsed with 2-3 mL acetonitrile/toluene solution, and cleaning solution is decanted to the purification column, repeating 2 to 3 times. The purification column was connected with a 25 mL reservoir and eluted with 25-30 mL of acetonitrile/toluene solution. The entire volume of effluent is collected and concentrated to 0.5 mL, and then evaporated to dryness by nitrogen. Finally, after adding 1 mL of ethyl acetate solution, it is dissolved by sonication and filter through a 0.22 μm nylon membrane.

Beneficial Effects of the Present Invention

1. The present invention establishes the corresponding electronic ID under the detection condition of GC-Q-Orbitrap according to each pesticide compound, and innovatively utilizes the unique retention index information of each pesticide in the establishment of the electronic ID to assist the confirmation of the pesticide compound. The accuracy and reliability of electronic ID is greatly increased.

2. The unique electronic ID information of each pesticide has been established in this invention. The electronic ID information comprises pesticide compound information, retention time, mass spectrum, and fragment ions information. In order to increase the precision and operability of the comparison, the optimized fragment ions are selected as the comparison basis. The core comparison fragment ion information is determined by the setting of the base peak ion. The technical solution of the present invention makes it unnecessary to prepare pesticide standards in food pesticide detection, and replaces the traditional identification method using pesticide materials standard as control with the electronic standard screening method to realize high-precision, high-efficiency and resource-saving non-target pesticide residue detection and achieve a leap in the development of pesticide residue detection technology.

3. The present invention has completed the extraction of electronic ID information of more than 600 pesticide compounds, and established a corresponding electronic ID database. The accuracy of 5 ppm is achieved based on the theoretical accurate mass number of the database. More important, multiple pesticide residue information could be acquired through one detection by GC-Q-Orbitrap on edible agro-products. Pesticide residue rapid screening and confirmation could be achieved by the comparison with the database. The sensitivity of 80% of the pesticides is lower than the uniform standard 10 μg/kg, it greatly decreases the false positive result and meets the requirement of various countries' pesticide residue MRLs.

4. It could effectively avoid the problem of inaccurate identification of pesticide compounds and isotopic peaks by using theoretical accurate mass number as fragment ion detection accurate mass number. The accuracy of the whole detection is improved, and the inaccurate detection result caused by the interference of the instrument is reduced. The theoretical derivation method adopted by theoretical accurate mass comprehensively utilizes the pesticide compound molecular cracking mechanism, it can greatly improve the accuracy of electronic ID and database establishment, increase the detection precision.

5. The present invention introduces the fragment ions selection model, realizes the rapid automatic selection of fragment ions. At the same time, it also introduces the intelligent matching model, calculates the intelligent matching value of each compound for quickly auto-comparison. The Intelligent matching values take into account the accurate mass number and ion abundance ratio and highlight the influences of ion fragments with relatively big differences based on the ion abundance ratios of base peak ions and variations of different confirmation ions, changing the original insufficient human judgment through the introduction of intelligent matching values, hence realizing accurate auto-matching and genuine automation of detection.

BRIEF DESCRIPTION OF DRAWINGS

FIG. 4 shows the first level mass spectrum of the peak in Dicofol solvent standard at 27.40 min

EMBODIMENTS

This invention will be presented in details with reference to figures and embodiments.

Figure 1:
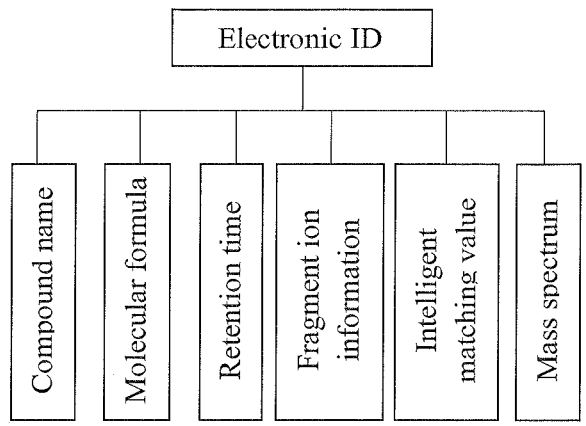
FIG. 1 shows GC-Q-Orbitrap pesticide compound electronic ID database model.

GC-Q-Orbitrap pesticide compound electronic ID database model is shown in FIG. 1, which comprises electronic ID of various pesticide compounds. The electronic ID comprises pesticide compound information, retention time, mass spectrum, fragment ion information, and intelligent matching value.

Next, Dicofol will be presented as an example to show the establishment process of pesticide compound electronic ID in details:

Chromatographic conditions: GC column is TG-5SILMS, 30 m×0.25 mm (i.d.)×0.25 μm. Temperature-programmed process: 40° C., kept for 1 minute; raised to 130° C. at 30° C./minute; raised to 250° C. at 5° C./minute; raised to 300° C. at 10° C./minute, and kept for 5 minutes; carrier gas: helium, purity 99.999%; flow rate: 1.2 mL/minute; injection port type: PTV; injection volume: 1 μL; injection method: temperature programmed injection, splitless time 1.5 minutes.

Mass spectrometry condition: EI source voltage: 70 eV; ion source temperature: 230° C.; transmission line temperature: 280° C.; solvent delay: 4 minutes; scan mode: full MS; mass scan range: 50-600 m/z; resolution: 60,000 FHWM (200 m/z); heptachlor epoxide is used to adjust retention time. Data acquisition is conducted by TraceFinder (Version. 4.0).

Figure 2:
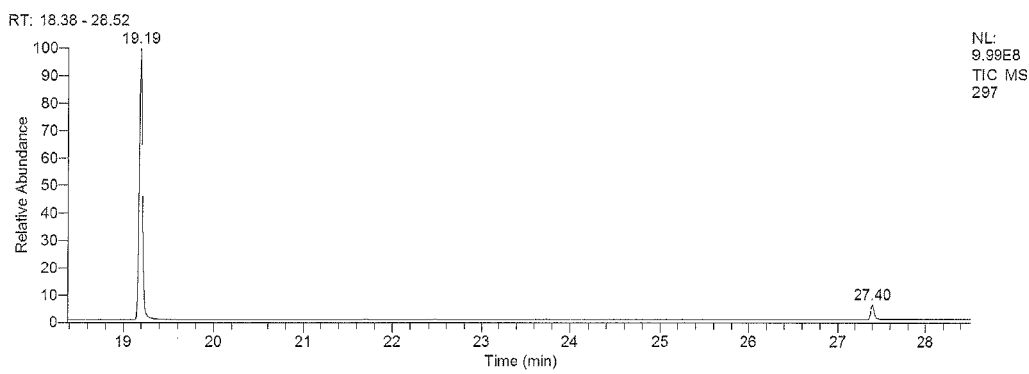
FIG. 2 shows total ion chromatography (TIC) of Dicofol solvent standard.
Figure 3:
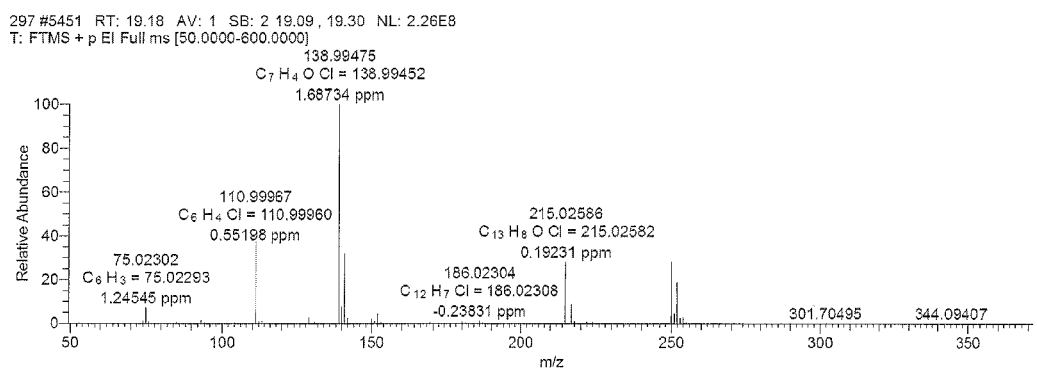
FIG. 3 shows the first level mass spectrum of the peak in Dicofol solvent standard at 19.19 min

PTV mode injection is adopted, the solvent standard is run under Full MS mode, and its molecular formula is $C_{14}H_9Cl_5O$. Total ion chromatography (TIC) of Dicofol solvent standard is shown as FIG. 2. There are two peaks shown in chromatography, the retention times are 19.19 min and 27.40 min respectively. Comparing the mass spectrum at 19.19 min and 27.40 min, it is found that ionic type and ionic abundance are very similar although their retention times are different. It cannot distinguish and identify them by ion element composition and accurate mass number. Then retention index is added as judgment assistance. Through calculation, the retention indexes of peak at 19.19 min and 27.40 min are 1995 and 2476, respectively. It is found that the retention index of Dicofol is 2467 in the existing data, which is close to that of the peak at 27.40 min, so the retention time of Dicofol is 27.40 min. It is inferred 5 $MS^1$ fragments are 138.99464, 140.99152, 215.02583, 251.00265 and 249.99475 respectively at 27.40 min Combined with its chemical structure and formula information, the theoretical accurate values of 5 $MS^1$ fragments are determined, they are base peak ion $C_7ClH_4O$ (138.99452, abundance 100.0), confirmation ions $C_7{}^{37}ClH_4O$ (140.99157, abundance 33.2), $C_{13}ClH_8O$ (215.02582, abundance 17.9), $C_{13}Cl_2H_9O$ (251.00250, abundance 29.9) and $C_{13}H_8OCl_2$ (249.99469, abundance 19.6). The mass errors of these 5 ions are all lower than 2 ppm. According to the fragment ions calculation, the intelligent matching value is 183.07860. Here is the calculation:

$$P_m = 0.5 \times 138.99452 + $$
$$0.5 \times \left( \frac{33.2 - 29.9}{33.2 - 17.9} \times 140.99157 + \frac{29.9 - 19.6}{33.2 - 17.9} \times 251.00250 + \frac{19.6 - 17.9}{33.2 - 17.9} \times 249.99469 \right) = 183.07860$$

As shown in FIG. 1, the theoretical accurate mass number of Dicofol and accurate mass number of its fragment ions are imported into the software to build accurate mass number database, and the confirmed first level mass spectrum is also imported into the spectrum library. The above retention time information and first level mass spectrometry information constitute electronic ID of Dicofol.

Figure 5:
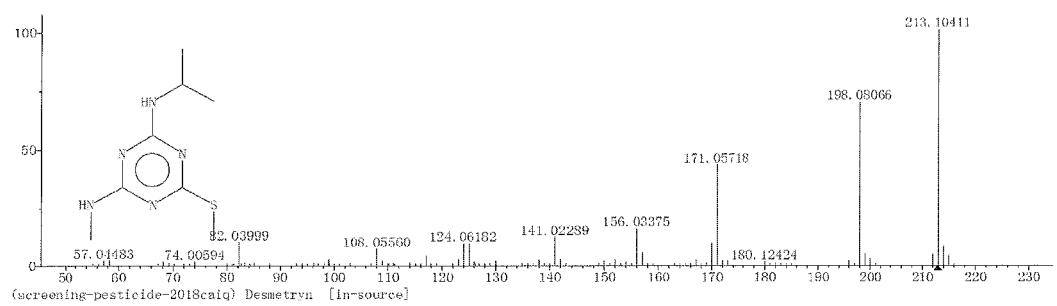
FIG. 5 shows mass spectrum examples of 5 representative pesticides in GC-Q-Orbitrap high-resolution mass spectrum database.

Through the above embodiment, the present invention performs plenty of experimental verification work, establishes the electronic ID database of over 600 pesticides commonly used in the world, and realizes the replacement of pesticide material standards by electronic standards. This method optimizes and determines the parameters and conditions of pesticide residues screening by GC-Q-Orbitrap, realizes the automatic comparison between test result and pesticide electronic ID database. This process achieves high speed (40 minutes), high-throughput (over 600 pesticides), high precision (0.00001 m/z), high reliability (over 6 confirmation points), high informatization and automation. Meanwhile, through one sample preparation, over 600 pesticide residues in edible agro-products can be rapidly screened by GC-Q-Orbitrap at the same time, thus achieving multi-indicators, non-targets, rapid screening of pesticide residues in edible agricultural products and significantly improving the discovery ability and method efficiency of this technique. Table 1 lists the examples of 5 representative pesticide compounds electronic ID in GC-Q-Orbitrap accurate mass number database. The mass spectrum in GC-Q-Orbitrap library are shown in FIG. 5. Table 2 lists over 600 pesticides in GC-Q-Orbitrap electronic ID database.

TABLE 1

Examples of 5 pesticide compounds electronic ID by GC-Q-Orbitrap

| No. | Compound Name | Type | MS Order | m/z | $P_m$ | Target Ratio (%) | Adduct | Retention Time |
|---|---|---|---|---|---|---|---|---|
| 1 | 1-Naphthyl Acetamide | TargetPeak | ms1 | 141.06988 | 137.1567 | | M+ | 17.88 |
| | 1-Naphthyl Acetamide | Confirming | ms1 | 185.08352 | | 41.07 | M+ | 17.88 |
| | 1-Naphthyl Acetamide | Confirming | ms1 | 142.0777 | | 52.95 | M+ | 17.88 |
| | 1-Naphthyl Acetamide | Confirming | ms1 | 115.05423 | | 36.67 | M+ | 17.88 |
| | 1-Naphthyl Acetamide | Confirming | ms1 | 139.05423 | | 18.36 | M+ | 17.88 |
| 2 | Atrazine | TargetPeak | ms1 | 200.06975 | 198.09524 | | M+ | 14.48 |
| | Atrazine | Confirming | ms1 | 202.0668 | | 32.73 | M+ | 14.48 |
| | Atrazine | Confirming | ms1 | 215.09322 | | 43.44 | M+ | 14.48 |
| | Atrazine | Confirming | ms1 | 173.04627 | | 26.04 | M+ | 14.48 |
| | Atrazine | Confirming | ms1 | 138.07742 | | 15.51 | M+ | 14.48 |
| 3 | Bifenox | TargetPeak | ms1 | 340.98523 | 301.53616 | | M+ | 27.68 |
| | Bifenox | Confirming | ms1 | 173.01525 | | 55.35 | M+ | 27.68 |
| | Bifenox | Confirming | ms1 | 342.98228 | | 63.42 | M+ | 27.68 |
| | Bifenox | Confirming | ms1 | 309.96684 | | 42.21 | M+ | 27.68 |
| | Bifenox | Confirming | ms1 | 189.01017 | | 31.4 | M+ | 27.68 |
| 4 | Cadusafos | TargetPeak | ms1 | 158.96978 | 169.4646 | | M+ | 13.28 |
| | Cadusafos | Confirming | ms1 | 213.01673 | | 32.93 | M+ | 13.28 |
| | Cadusafos | Confirming | ms1 | 157.96196 | | 43.13 | M+ | 13.28 |
| | Cadusafos | Confirming | ms1 | 126.99771 | | 25.71 | M+ | 13.28 |
| | Cadusafos | Confirming | ms1 | 130.93848 | | 25.44 | M+ | 13.28 |
| 5 | Desmetryn | TargetPeak | ms1 | 213.10427 | 197.90374 | | M+ | 16.71 |
| | Desmetryn | Confirming | ms1 | 171.05732 | | 42.71 | M+ | 16.71 |
| | Desmetryn | Confirming | ms1 | 198.08079 | | 69.13 | M+ | 16.71 |
| | Desmetryn | Confirming | ms1 | 156.03384 | | 15.45 | M+ | 16.71 |
| | Desmetryn | Confirming | ms1 | 141.02294 | | 12.12 | M+ | 16.71 |

(excluding mass spectrum and molecular formula)

TABLE 2

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 1 | 1,4-Dimethylnaphthalene | 1,4-二甲基萘 | C12H12 | 156.0939 | 571-58-4 | 9.12 |
| 2 | 1-naphthylacetic acid | 1-萘乙酸 | C13H12O2 | 200.08373 | 86-87-3 | 13.59 |
| 3 | 1-Naphthyl Acetamide | 萘乙酰胺 | C12H11NO | 185.08406 | 86-86-2 | 17.88 |
| 4 | 2,3,4,5-Tetrachloroaniline | 2,3,4,5-四氯苯胺 | C6H3Cl4N | 228.90196 | 634-83-3 | 14.89 |
| 5 | 2,3,4,5-Tetrachloroanisole | 2,3,4,5-四氯甲氧基苯 | C7H4Cl4O | 243.90163 | 938-86-3 | 12.71 |
| 6 | 2,3,5,6-Tetrachloroaniline | 2,3,5,6-四氯苯胺 | C6H3Cl4N | 228.90196 | 3481-20-7 | 12.13 |
| 7 | 2.3.5-Trimethacarb | 2,3,5-混杀威 | C11H15NO2 | 193.11028 | 2655-15-4 | 12.64 |
| 8 | De-Pcb 31 2,4',5-Trichlorobiphenyl | 2,4',5-三氯联苯醚 | C12H7Cl3 | 255.96133 | 16606-02-3 | 16.85 |
| 9 | 2,4,6-Trichlorophenol | 2,4,6-三氯苯酚 | C6H3Cl3O | 195.92495 | 88-06-2 | 7.8 |
| 10 | 2,4-D-ethylhexyl | 2,4-滴异辛酯 | C16H22Cl2O3 | 332.0946 | 1928-43-4 | 22.72 |
| 11 | 2,4-D butylate | 2,4-滴丁酯 | C12H14Cl2O3 | 276.032 | 94-80-4 | 17.03 |
| 12 | 2,4-DB | 4-(2,4-二氯苯氧基)丁酸 | C11H12Cl2O3 | 262.01635 | 94-82-6 | 16.44 |
| 13 | 2,6-Dichlorobenzamide | 2,6-二氯苯甲酰胺 | C7H5Cl2NO | 188.97482 | 2008-58-4 | 12.8 |
| 14 | 2-Phenylphenol | 邻苯基苯酚 | C12H10O | 170.07317 | 90-43-7 | 10.31 |
| 15 | 3,4,5-Trimethacarb | 3,4,5-三甲威 | C11H15NO2 | 193.11028 | 2686-99-9 | 14.09 |
| 16 | 3,5-Dichloroaniline | 3,5-二氯苯胺 | C6H5Cl2N | 160.9799 | 626-43-7 | 8.45 |
| 17 | 3-Chloro-4-Methylaniline | 3-氯对甲苯胺 | C7H8ClN | 141.03453 | 95-74-9 | 7.05 |
| 18 | 3-Phenylphenol | 3-苯基苯酚 | C12H10O | 170.07317 | 580-51-8 | 13.69 |
| 19 | 4,4'-DDE | p,p'-滴滴伊 | C14H8Cl4 | 315.93801 | 72-55-9 | 22.39 |
| 20 | 4,4'-Dibromobenzophenone | 4,4-二溴二苯甲酮 | C13H8Br2O | 337.89419 | 3988-03-2 | 23.12 |
| 21 | 4,4'-Dichlorobenzophenone | 4,4-二氯二苯甲酮 | C13H8Cl2O | 249.99522 | 90-98-2 | 19.19 |
| 22 | 4-Bromo-3,5-Dimethylphenyl-N-Methylcarbamate | 4-溴-3,5-二甲基苯-N-甲基氨基甲酸酯 | C10H12BrNO2 | 257.00514 | 672-99-1 | 9.57 |
| 23 | 4-Chloronitrobenzene | 4-氯硝基苯 | C6H4ClNO2 | 156.99306 | 100-00-5 | 6.49 |
| 24 | 4-Chlorophenoxyacetic acid | 4-氯苯氧基乙酸 | C9H9ClO3 | 200.02402 | 122-88-3 | 9.74 |
| 25 | 8-hydroxyquinoline | 8-羟基喹啉 | C9H7NO | 145.05276 | 148-24-3 | 7.94 |
| 26 | Acenaphthene | 戒杀灵 | C12H10 | 154.07825 | 83-32-9 | 9.91 |
| 27 | Acetochlor | 乙草胺 | C14H20ClNO2 | 269.11826 | 34256-82-1 | 16.9 |
| 28 | Acibenzolar-S-methyl | 阿拉酸式-S-甲基 | C8H6N2OS2 | 209.99216 | 135158-54-2 | 17.37 |
| 29 | Aclonifen | 苯草醚 | C12H9ClN2O3 | 264.03017 | 74070-46-5 | 23.98 |
| 30 | Acrinathrin | 氟丙菊酯 | C26H21F6NO5 | 541.13239 | 101007-06-1 | 29.05 |
| 31 | Akton | 硫虫设 | C12H14Cl3O3PS | 373.94669 | 1757-18-2 | 21.21 |
| 32 | Alachlor | 甲草胺 | C14H20ClNO2 | 269.11826 | 15972-60-8 | 17.2 |
| 33 | Alanycarb | 棉铃威 | C17H25N3O4S2 | 399.12865 | 83130-01-2 | 11.88 |
| 34 | Aldimorph | 4-十二烷基-2,6-二甲基吗啉 | C18H37NO | 283.28752 | 91315-15-0 | 18.13 |
| 35 | Aldrin | 艾氏剂 | C12H8Cl6 | 361.87572 | 309-00-2 | 18.7 |
| 36 | Allethrin | 烯丙菊酯 | C19H26O3 | 302.18819 | 584-79-2 | 20.59 |
| 37 | Allidochlor | 二丙烯草胺 | C8H12ClNO | 173.06074 | 93-71-0 | 6.87 |
| 38 | alpha-Cypermethrin | 顺式氯氰菊酯 | C22H19Cl2NO3 | 415.0742 | 67375-30-8 | 31.51 |
| 39 | alpha-Endosulfan | α-硫丹 | C9H6Cl6O3S | 403.81688 | 959-98-8 | 21.5 |
| 40 | Ametryn | 莠灭净 | C9H17N5S | 227.12047 | 834-12-8 | 17.52 |
| 41 | Amidosulfuron | 酰嘧磺隆 | C9H15N5O7S2 | 369.04129 | 120923-37-7 | 7.34 |
| 42 | Aminocarb | 杀虫威 | C11H16N2O2 | 208.12118 | 2032-59-9 | 14.77 |
| 43 | Amisulbrom | 吲唑磺菌胺 | C13H13BrFN5O4S2 | 464.95764 | 348635-87-0 | 30.8 |
| 44 | Ancymidol | 环丙嘧啶醇 | C15H16N2O2 | 256.12118 | 12771-68-5 | 23.34 |
| 45 | Anilofos | 莎稗磷 | C13H19ClNO3PS2 | 367.02325 | 64249-01-0 | 27.64 |
| 46 | Anthracene D10 | 蒽-D10 | C14D10 | 188.14102 | 1719-06-8 | 15.39 |
| 47 | Aramite | 杀螨特 | C15H23ClO4S | 334.10056 | 140-57-8 | 22.83 |
| 48 | Aspon | 丙硫特普 | C12H28O5P2S2 | 378.08534 | 3244-90-4 | 18.6 |
| 49 | Atraton | 阿特拉通 | C9H17N5O | 211.14331 | 1610-17-9 | 14.09 |
| 50 | Atrazine | 阿特拉津 | C8H14ClN5 | 215.09377 | 1912-24-9 | 14.48 |
| 51 | Atrazine-desethyl | 脱乙基阿特拉津 | C6H10ClN5 | 187.06247 | 6190-65-4 | 12.69 |
| 52 | Atrazine-desisopropyl | 氟氯氢菊酯 | C5H8ClN5 | 173.04682 | 1007-28-9 | 12.49 |
| 53 | Azaconazole | 氯环唑 | C12H11Cl2N3O2 | 299.02283 | 60207-31-0 | 22.75 |
| 54 | Azinphos-ethyl | 益棉磷 | C12H16N3O3PS2 | 345.03707 | 2642-71-9 | 29.39 |
| 55 | Azinphos-methyl | 保棉磷 | C10H12N3O3PS2 | 317.00577 | 86-50-0 | 28.29 |
| 56 | Aziprotryne | 盘氰净 | C7H11N7S | 225.07966 | 4658-28-0 | 15.58 |
| 57 | Azoxystrobin | 咪菌酯 | C22H17N3O5 | 403.11682 | 131860-33-8 | 33.78 |
| 58 | Barban | 燕麦灵 | C11H9Cl2NO2 | 257.00103 | 101-27-9 | 22.53 |
| 59 | Beflubutamid | 氟丁酰草胺 | C18H17F4NO2 | 355.11954 | 113614-08-7 | 20.63 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 60 | Benalaxyl | 苯霜灵 | C20H23NO3 | 325.16779 | 71626-11-4 | 24.77 |
| 61 | Benazolin-ethyl | 草除灵 | C11H10ClNO3S | 271.00699 | 25059-80-7 | 20.11 |
| 62 | Bendiocarb | 噁虫威 | C11H13NO4 | 223.08446 | 22781-23-3 | 12.98 |
| 63 | Benfluralin | 乙丁氟灵 | C13H16F3N3O4 | 335.10929 | 1861-40-1 | 13.02 |
| 64 | Benfuracarb | 丙扁克白威 (frozen) | C20H30N2O5S | 410.18754 | 82560-54-1 | 29.36 |
| 65 | Benfuresate | 呋草黄 | C12H16O4S | 256.07693 | 68505-69-1 | 16.63 |
| 66 | Benodanil | 麦锈灵 | C13H10INO | 322.98071 | 15310-01-7 | 24.18 |
| 67 | Benoxacor | 解草嗪 | C11H11Cl2NO2 | 259.01668 | 98730-04-2 | 16.23 |
| 68 | Benzoximate | 苯螨特 | C18H18ClNO5 | 363.08735 | 29104-30-1 | 27.38 |
| 69 | Benzoylprop-Ethyl | 新燕灵 | C18H17Cl2NO3 | 365.05855 | 22212-55-1 | 26.5 |
| 70 | beta-Endosulfan | β-β-硫丹 | C9H6Cl6O3S | 403.81688 | 33213-65-9 | 23.63 |
| 71 | Bifenazate | 联苯肼酯 | C17H20N2O3 | 300.14739 | 149877-41-8 | 27.3 |
| 72 | Bifenox | 治草醚 | C14H9Cl2NO5 | 340.98578 | 42576-02-3 | 27.68 |
| 73 | Bifenthrin | 联苯菊酯 | C23H22ClF3O2 | 422.12604 | 82657-04-3 | 27.17 |
| 74 | Binapacryl | 乐杀螨 | C15H18N2O6 | 322.11649 | 485-31-4 | 23.06 |
| 75 | Bioresmethrin | 生物苄呋菊酯 | C22H26O3 | 338.18819 | 28434-01-7 | 26.33 |
| 76 | Biphenyl | 联苯 | C12H10 | 154.07825 | 92-52-4 | 8.24 |
| 77 | Bitertanol | 联苯三唑醇 | C20H23N3O2 | 337.17903 | 55179-31-2 | 30.11 |
| 78 | Boscalid | 啶酰菌胺 | C18H12Cl2N2O | 342.03267 | 188425-85-6 | 31.49 |
| 79 | Bromacil | 除草定 | C9H13BrN2O2 | 260.01604 | 314-40-9 | 18.14 |
| 80 | Bromfenvinfos | 溴芬松 | C12H14BrCl2O4P | 401.91901 | 33399-00-7 | 21.78 |
| 81 | Bromfenvinfos-Methyl | 甲基溴芬松 | C10H10BrCl2O4P | 373.88771 | 13104-21-7 | 20.31 |
| 82 | Bromobutide 	 | 溴丁酰草胺 | C15H22BrNO | 311.08848 | 74712-19-9 | 16.88 |
| 83 | Bromocyclen | 澳西林 | C8H5BrCl6 | 389.77058 | 1715-40-8 | 16.17 |
| 84 | Bromophos-Ethyl | 乙基溴硫磷 | C10H12BrCl2O3PS | 391.88052 | 4824-78-6 | 21.08 |
| 85 | Bromophos-Methyl | 溴硫磷 | C8H8BrCl2O3PS | 363.84922 | 2104-96-3 | 19.49 |
| 86 | Bromopropylate | 溴螨酯 | C17H16Br2O3 | 425.94662 | 18181-80-1 | 27.12 |
| 87 | Bromoxynil octanoate | 辛酰溴苯腈 | C15H17Br2NO2 | 400.9626 | 1689-99-2 | 24.98 |
| 88 | Bromuconazole | 粉菌唑 | C13H12BrCl2N3O | 374.95408 | 116255-48-2 | 27.65 |
| 89 | Bupirimate | 乙嘧酚磺酸酯 | C13H24N4O3S | 316.15691 | 41483-43-6 | 22.74 |
| 90 | Buprofezin | 噻嗪酮 | C16H23N3OS | 305.15618 | 69327-76-0 | 22.71 |
| 91 | Butachlor | 丁草胺 | C17H26ClNO2 | 311.16521 | 23184-66-9 | 21.46 |
| 92 | Butafenacil | 氟丙嘧草酯 | C20H18ClF3N2O6 | 474.08055 | 134605-64-4 | 30.76 |
| 93 | Butamifos | 抑草磷 | C13H21N2O4PS | 332.09596 | 36335-67-8 | 21.68 |
| 94 | Butralin | 仲丁灵 | C14H21N3O4 | 295.15321 | 33629-47-9 | 19.42 |
| 95 | Buturon | 炔草隆 | C12H13ClN2O | 236.07164 | 3766-60-7 | 19.23 |
| 96 | Butylate | 丁草特/丁烷敌 | C11H23NOS | 217.15004 | 2008-41-5 | 8.78 |
| 97 | Cadusafos | 硫线磷 | C10H23O2PS2 | 270.08771 | 95465-99-9 | 13.28 |
| 98 | Cafenstrole | 唑草胺 | C16H22N4O3S | 350.14126 | 125306-83-4 | 30.86 |
| 99 | Captafol | 敌菌丹 | C10H9Cl4NO2S | 346.91081 | 2425-06-1 | 25.98 |
| 100 | Captan | 克菌丹 | C9H8Cl3NO2S | 298.93413 | 133-06-2 | 20.46 |
| 101 | Carbaryl | 甲萘威 | C12H11NO2 | 201.07898 | 63-25-2 | 17.3 |
| 102 | Carbofuran | 克百威 | C12H15NO3 | 221.10519 | 1563-66-2 | 14.25 |
| 103 | Carbofuran-3-Hydroxy | 三羟基克百威 | C12H15NO4 | 237.10011 | 16655-82-6 | 16.21 |
| 104 | Carbophenothion | 三硫磷 | C11H16ClO2PS3 | 341.97386 | 786-19-6 | 24.86 |
| 105 | Carbosulfan | 丁硫百威 | C20H32N2O3S | 380.21336 | 55285-14-8 | 26.8 |
| 106 | Carboxin | 萎锈灵 | C12H13NO2S | 235.0667 | 5234-68-4 | 22.68 |
| 107 | Carfentrazone-ethyl | 唑酮酯 | C15H14Cl2F3N3O3 | 411.03643 | 128639-02-1 | 24.83 |
| 108 | Chinomethionat | 灭螨猛 | C10H6N2OS2 | 233.99216 | 2439-01-2 | 21.01 |
| 109 | Chlorbenside | 氯杀螨 | C13H10Cl2S | 267.98803 | 103-17-3 | 21 |
| 110 | Chlorbenside sulfone | 毒虫畏 | C13H10Cl2O2S | 299.97786 | 7082-99-7 | 24.71 |
| 111 | Chlorbromuron | 氯溴隆 | C9H10BrClN2O2 | 291.96142 | 13360-45-7 | 20.23 |
| 112 | Chlorbufam | 氯炔灵 | C11H10ClNO2 | 223.04001 | 1967-16-4 | 14.53 |
| 113 | Chlordane | 氯丹 | C10H6Cl8 | 405.79777 | 57-74-9 | 21.02 |
| 114 | Chlordimeform | 杀虫脒 | C10H13ClN2 | 196.07673 | 6164-98-3 | 12.73 |
| 115 | Chlorethoxyfos | 氯氧磷 | C6H11Cl4O3PS | 333.89206 | 54593-83-8 | 11.99 |
| 116 | Chlorfenapyr | 虫螨腈 | C15H11BrClF3N2O | 405.96954 | 122453-73-0 | 23.07 |
| 117 | Chlorfenethol | 杀螨醇 | C14H12Cl2O | 266.02652 | 80-06-8 | 20.41 |
| 118 | Chlorfenprop-Methyl | 燕麦酯 | C10H10Cl2O2 | 232.00579 | 14437-17-3 | 11.56 |
| 119 | Chlorfenson | 杀螨酯 | C12H8Cl2O3S | 301.95712 | 80-33-1 | 21.91 |
| 120 | Chlorfenvinphos | 虫螨腈 | C12H14Cl3O4P | 357.96953 | 470-90-6 | 20.34 |
| 121 | Chlorfluazuron | 氟啶脲 | C20H9Cl3F5N3O3 | 538.96297 | 71422-67-8 | 21.73 |
| 122 | Chlorflurenol-methyl | 整形素 | C15H11ClO3 | 274.03967 | 2536-31-4 | 20.81 |
| 123 | Chloridazon | 氯草敏 | C10H8ClN3O | 221.03559 | 1698-60-8 | 25.18 |
| 124 | Chlormephos | 氯甲磷 | C5H12ClO2PS2 | 233.97049 | 24934-91-6 | 8.92 |
| 125 | Chlorbenzilate | 乙酯杀螨醇 | C16H14Cl2O3 | 324.032 | 510-15-6 | 23.63 |
| 126 | Chloroneb | 地茂散 | C8H8Cl2O2 | 205.99014 | 2675-77-6 | 10.02 |
| 127 | Chloropropylate | 丙酯杀螨醇 | C17H16Cl2O3 | 338.04765 | 5836-10-2 | 23.59 |
| 128 | Chlorothalonil | 百菌清 | C8Cl4N2 | 263.88156 | 1897-45-6 | 15.33 |
| 129 | chlorotoluron | 绿麦隆 | C10H13ClN2O | 212.07164 | 15545-48-9 | 18.38 |
| 130 | Chlorpropham | 氯苯胺灵 | C10H12ClNO2 | 213.05566 | 101-21-3 | 12.73 |
| 131 | Chlorpyrifos | 毒死蜱 | C9H11Cl3NO3PS | 348.92629 | 2921-88-2 | 18.72 |
| 132 | Chlorpyrifos-methyl | 甲基毒死蜱 | C7H7Cl3NO3PS | 320.89498 | 5598-13-0 | 16.94 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 133 | Chlorpyrifos-oxon | 氯毒死蜱 | C9H11Cl3NO4P | 332.94913 | 5598-15-2 | 18.48 |
| 134 | Chlorsulfuron | 氯磺隆 | C12H12ClN5O4S | 357.02985 | 64902-72-3 | 6.9 |
| 135 | Chlorthal-dimethyl | 氯酞酸二甲酯 | C10H6Cl4O4 | 329.90202 | 1861-32-1 | 18.83 |
| 136 | Chlorthiamid | 草克乐 | C7H5Cl2NS | 204.95198 | 1918-13-4 | 16.63 |
| 137 | Chlorthion | 氯硫磷 | C8H9ClNO5PS | 296.96276 | 500-28-7 | 19.23 |
| 138 | Chlorthiophos | 虫螨磷 | C11H15Cl2O3PS2 | 359.95773 | 60238-56-4 | 24.1 |
| 139 | Chlozolinate | 乙菌利 | C13H11Cl2NO5 | 331.00143 | 84332-86-5 | 19.54 |
| 140 | Cinidon-Ethyl | 吲哚酮草酯 | C19H17Cl2NO4 | 393.05346 | 142891-20-1 | 34.95 |
| 141 | cis-1,2,3,6-Tetrahydrophthalimide | 1,2,3,6-四氢邻苯二甲酰亚胺 | C8H9NO2 | 151.06333 | 1469-48-3 | 9.79 |
| 142 | Cis-Chlordane (alpha) | 顺式氯丹 | C10H6Cl8 | 405.79777 | 5103-71-9 | 21.5 |
| 143 | cis-Permethrin | 顺式-氯菊酯 | C21H20Cl2O3 | 390.07895 | 61949-76-6 | 30.27 |
| 144 | Clodinafop | 炔草酸 | C14H11ClFNO4 | 311.03606 | 114420-56-3 | 22.82 |
| 145 | Clodinafop-propargyl | 炔草酯 | C17H13ClFNO4 | 349.05171 | 105512-06-9 | 25.39 |
| 146 | Clomazone | 异噁草松 | C12H14ClNO2 | 239.07131 | 81777-89-1 | 14.58 |
| 147 | Clopyralid | 异恶草松 | C7H5Cl2NO2 | 204.96973 | 1702-17-6 | 9.09 |
| 148 | Chlordecone | 火蚁灵 | C10Cl10O | 485.68344 | 143-50-0 | 24.55 |
| 149 | Coumaphos | 蝇毒磷 | C14H16ClO5PS | 362.01446 | 56-72-4 | 30.37 |
| 150 | coumaphos-oxon | 蝇毒磷 | C14H16ClO6P | 346.0373 | 321-54-0 | 29.49 |
| 151 | Crimidine | 鼠立死 | C7H10ClN3 | 171.05633 | 535-89-7 | 10.09 |
| 152 | Crotoxyphos | 巴毒磷 | C14H19O6P | 314.09193 | 7700-17-6 | 20.82 |
| 153 | Crufomate | 育磷 | C12H19ClNO3P | 291.07911 | 299-86-5 | 19.35 |
| 154 | Cyanazine | 氰草津 | C9H13ClN6 | 240.08902 | 21725-46-2 | 18.82 |
| 155 | Cyanofenphos | 苯腈磷 | C15H14NO2PS | 303.04829 | 13067-93-1 | 24.91 |
| 156 | Cyanophos | 杀螟腈 | C9H10NO3PS | 243.0119 | 2636-26-2 | 14.92 |
| 157 | Cycloate | 环草敌 | C11H21NOS | 215.13439 | 1134-23-2 | 12.37 |
| 158 | Cycloprothrin | 乙氰菊酯 | C26H21Cl2NO4 | 481.08476 | 63935-38-6 | 16.73 |
| 159 | Cycluron | 环莠隆 | C11H22N2O | 198.17321 | 2163-69-1 | 14.9 |
| 160 | Cyenopyrafen | 腈吡螨酯 | C24H31N3O2 | 393.24163 | 560121-52-0 | 27.64 |
| 161 | Cyflufenamid | 环氟菌胺 | C20H17F5N2O2 | 412.12102 | 180409-60-3 | 23.13 |
| 162 | Cyfluthrin | 氟氯氰菊酯 | C22H18Cl2FNO3 | 433.06478 | 68359-37-5 | 31.06 |
| 163 | Cyhalofop-Butyl | 氰氟草酯 | C20H20FNO4 | 357.13764 | 122008-85-9 | 28.73 |
| 164 | Cymiazole | 蜱螨胺 | C12H14N2S | 218.08777 | 61676-87-7 | 17.3 |
| 165 | Cypermethrin | 氯氰菊酯 | C22H19Cl2NO3 | 415.0742 | 52315-07-8 | 31.65 |
| 166 | Cyphenothrin | 苯氧菊酯 | C24H25NO3 | 375.18344 | 39515-40-7 | 29.89 |
| 167 | Cyprazine | 环丙津 | C9H14ClN5 | 227.09377 | 22936-86-3 | 16.87 |
| 168 | Cyproconazole | 环丙唑醇 | C15H18ClN3O | 291.11384 | 94361-06-5 | 23.11 |
| 169 | Cyprodinil | 嘧菌环胺 | C14H15N3 | 225.1266 | 121552-61-2 | 19.95 |
| 170 | Cyprofuram | 酯菌胺 | C14H14ClNO3 | 279.06622 | 69581-33-5 | 23.62 |
| 171 | Cyromazine | 灭蝇胺 | C6H10N6 | 166.09669 | 66215-27-8 | 14.5 |
| 172 | Dazomet | 棉隆 | C5H10N2S2 | 162.02854 | 533-74-4 | 13.84 |
| 173 | 2,4'-DDD | o,p'-滴滴滴 | C14H10Cl4 | 317.95366 | 53-19-0 | 22.63 |
| 174 | 4,4'-DDD | p,p'-滴滴滴 | C14H10Cl4 | 317.95366 | 72-54-8 | 23.88 |
| 175 | 2,4'-DDE | o,p'-滴滴伊 | C14H8Cl4 | 315.93801 | 3424-82-6 | 21.16 |
| 176 | 2,4'-DDT | o,p'-滴滴涕 | C14H9Cl5 | 351.91469 | 789-02-6 | 23.96 |
| 177 | DDT | p,p'-滴滴涕 | C14H9Cl5 | 351.91469 | 50-29-3 | 25.27 |
| 178 | Deltamethrin | 溴氰菊酯 | C22H19Br2NO3 | 502.97317 | 52918-63-5 | 33.58 |
| 179 | Demeton-O | 内吸磷-O | C8H19O3PS2 | 258.05132 | 298-03-3 | 12.01 |
| 180 | Demeton-S | 内吸磷-S | C8H19O3PS2 | 258.05132 | 126-75-0 | 13.97 |
| 181 | Demeton-S-Methyl | 甲基内吸磷 | C6H15O3PS2 | 230.02002 | 919-86-8 | 12.04 |
| 182 | Desethylterbuthylazine | 去乙基特丁津 | C7H12ClN5 | 201.07812 | 30125-63-4 | 13.07 |
| 183 | Desmetryn | 敌草净 | C8H15N5S | 213.10482 | 1014-69-3 | 16.71 |
| 184 | Dialifos | 氧亚胺硫磷 | C14H17ClNO4PS2 | 393.00251 | 10311-84-9 | 29.51 |
| 185 | Diallate | 燕麦敌 | C10H17Cl2NOS | 269.04079 | 2303-16-4 | 13.44 |
| 186 | Diazinon | 二嗪农 | C12H21N2O3PS | 304.10105 | 333-41-5 | 15.28 |
| 187 | Dibutyl succinate | 驱虫特 | C12H22O4 | 230.15181 | 141-03-7 | 10.91 |
| 188 | Dicapthon | 异氯磷 | C8H9ClNO5PS | 296.96276 | 2463-84-5 | 19.04 |
| 189 | Dichlobenil | 敌草脂 | C7H3Cl2N | 170.96425 | 1194-65-6 | 7.63 |
| 190 | Dichlofenthion | 除线磷 | C10H13Cl2O3PS | 313.97001 | 97-17-6 | 16.69 |
| 191 | Dichlofluanid | 抑菌灵 | C9H11Cl2FN2O2S2 | 331.9623 | 1085-98-9 | 18.33 |
| 192 | Dichlormid | 二氯丙烯胺 | C8H11Cl2NO | 207.02177 | 37764-25-3 | 7.71 |
| 193 | Dichlorprop | 二氯丙酸 | C10H10Cl2O3 | 248.0007 | 120-36-5 | 11.88 |
| 194 | Dichlorvos | 敌敌畏 | C4H7Cl2O4P | 219.9459 | 62-73-7 | 6.37 |
| 195 | Diclobutrazol | 苯氯三唑醇 | C15H19Cl2N3O | 327.09052 | 75736-33-3 | 22.71 |
| 196 | Diclocymet | 双氯氰菌胺 | C15H18Cl2N2O | 312.07962 | 139920-32-4 | 20.48 |
| 197 | Diclofop-methyl | 禾草灵 | C16H14Cl2O4 | 340.02692 | 51338-27-3 | 25.88 |
| 198 | Dicloran | 氯硝胺 | C6H4Cl2N2O2 | 205.96498 | 99-30-9 | 13.99 |
| 199 | Dicofol | 三氯杀螨醇 | C14H9Cl5O | 367.9096 | 115-32-2 | 27.39 |
| 200 | Dicrotophos | 百治磷 | C8H16NO5P | 237.07661 | 141-66-2 | 12.77 |
| 201 | Dieldrin | 狄氏剂 | C12H8Cl6O | 377.87063 | 60-57-1 | 22.5 |
| 202 | Diethatyl-Ethyl | 乙酰甲草胺 | C16H22ClNO3 | 311.12882 | 38727-55-8 | 21.72 |
| 203 | Diethofencarb | 乙霉威 | C14H21NO4 | 267.14706 | 87130-20-9 | 18.86 |
| 204 | Diethyltoluamide | 避蚊胺 | C12H17NO | 191.13101 | 134-62-3 | 11.25 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 205 | Difenoconazole | 苯醚甲环唑 | C19H17Cl2N3O3 | 405.0647 | 119446-68-3 | 33.26 |
| 206 | Difenoxuron | 枯莠隆 | C16H18N2O3 | 286.13174 | 14214-32-5 | 18.88 |
| 207 | Diflufenican | 吡氟酰草胺 | C19H11F5N2O2 | 394.07407 | 83164-33-4 | 25.99 |
| 208 | Diflufenzopyr | 氟吡草腙钠盐 | C15H12F2N4O3 | 334.08775 | 109293-97-2 | 7.39 |
| 209 | Dimepiperate | 哌草丹 | C15H21NOS | 263.13439 | 61432-55-1 | 20.61 |
| 210 | Dimethachlor | 二甲草胺 | C13H18ClNO2 | 255.10261 | 50563-36-5 | 16.69 |
| 211 | Dimethametryn | 异戊乙净 | C11H21N5S | 255.15177 | 22936-75-0 | 20.17 |
| 212 | Dimethenamid | 二甲吩草胺 | C12H18ClNO2S | 275.07468 | 87674-68-8 | 16.72 |
| 213 | Dimethipin | 噻节因 | C6H10O4S2 | 210.00205 | 55290-64-7 | 14.39 |
| 214 | Dimethoate | 乐果 | C5H12NO3PS2 | 228.99962 | 60-51-5 | 13.96 |
| 215 | Dimethomorph | 烯酰吗啉 | C21H22ClNO4 | 387.12374 | 110488-70-5 | 34.38 |
| 216 | Dimethyl phthalate | 避蚊酯 | C10H10O4 | 194.05791 | 131-11-3 | 9.12 |
| 217 | Dimethylvinphos | 甲基毒虫畏 | C10H10Cl3O4P | 329.93823 | 71363-52-5 | 18.21 |
| 218 | Dimetilan | 敌蝇威 | C10H16N4O3 | 240.12224 | 644-64-4 | 17.37 |
| 219 | Diniconazole | 烯唑醇 | C15H17Cl2N3O | 325.07487 | 83657-24-3 | 23.74 |
| 220 | Dinitramine | 氮氟灵 | C11H13F3N4O4 | 322.08889 | 29091-05-2 | 15.65 |
| 221 | Dinobuton | 敌螨通 | C14H18N2O7 | 326.1114 | 973-21-7 | 20.51 |
| 222 | Dinoseb | 地乐酚 | C10H12N2O5 | 240.07462 | 88-85-7 | 15.52 |
| 223 | Dinoterb | 荔溶酚 | C10H12N2O5 | 240.07462 | 1420-07-1 | 15.15 |
| 224 | Diofenolan | 二苯丙醚 | C18H20O4 | 300.13616 | 63837-33-2 | 25.08 |
| 225 | Dioxabenzofos | 蔬果磷 | C8H9O3PS | 216.001 | 3811-49-2 | 12.94 |
| 226 | Dioxacarb | 二氧威 | C11H13NO4 | 223.08446 | 6988-21-2 | 8.63 |
| 227 | Dioxathion | 敌噁磷 | C12H26O6P2S4 | 456.00875 | 78-34-2 | 30.48 |
| 228 | Diphenamid | 双苯酰草胺 | C16H17NO | 239.13101 | 957-51-7 | 19.5 |
| 229 | Diphenylamine | 二苯胺 | C12H11N | 169.08915 | 122-39-4 | 12.17 |
| 230 | Dipropetryn | 异丙净 | C11H21N5S | 255.15177 | 4147-51-7 | 18.64 |
| 231 | Dipropyl Isocinchomeronate | 吡啶酸双丙酯 | C13H17NO4 | 251.11576 | 136-45-8 | 17.25 |
| 232 | Disulfoton | 乙拌磷 | C8H19O2PS3 | 274.02848 | 298-04-4 | 15.57 |
| 233 | Disulfoton sulfone | 乙拌磷砜 | C8H19O4PS3 | 306.01831 | 2497-06-5 | 21.39 |
| 234 | Disulfoton sulfoxide | 砜拌磷 | C8H19O3PS3 | 290.02339 | 2497-07-6 | 7.37 |
| 235 | Ditalimfos | 灭菌磷 | C12H14NO4PS | 299.03812 | 5131-24-8 | 21.63 |
| 236 | Dithiopyr | 氟硫草定 | C15H16F5NO2S2 | 401.05426 | 97886-45-8 | 17.81 |
| 237 | Dodemorph | 十二环吗啉 | C18H35NO | 281.27186 | 1593-77-7 | 19.58 |
| 238 | Drazoxolon | 肼菌酮 | C10H8ClN3O2 | 237.0305 | 5707-69-7 | 19.41 |
| 239 | Edifenphos | 敌瘟磷 | C14H15O2PS2 | 310.02511 | 17109-49-8 | 24.92 |
| 240 | Endosulfan-sulfate | 硫丹硫酸酯 | C9H6Cl6O4S | 419.8118 | 1031-07-8 | 25.03 |
| 241 | Endrin | 异狄氏剂 | C12H8Cl6O | 377.87063 | 72-20-8 | 23.19 |
| 242 | Endrin-aldehyde | 异狄氏剂醛 | C12H8Cl6O | 377.87063 | 7421-93-4 | 24.14 |
| 243 | Endrin-ketone | 异狄氏剂酮 | C12H8Cl6O | 377.87063 | 53494-70-5 | 26.65 |
| 244 | EPN | 苯硫磷 | C14H14NO4PS | 323.03812 | 2104-64-5 | 27.05 |
| 245 | Epoxiconazole | 氟环唑 | C17H13ClFN3O | 329.07312 | 133855-98-8 | 26.23 |
| 246 | EPTC | 扑草灭 | C9H19NOS | 189.11874 | 759-94-4 | 7.75 |
| 247 | Erbon | 抑草莲 | C11H9Cl5O3 | 363.89943 | 136-25-4 | 23.03 |
| 248 | Esprocarb | 禾草畏 | C15H23NOS | 265.15004 | 85785-20-2 | 18.39 |
| 249 | Ethalfluralin | 丁烯氟灵 | C13H14F3N3O4 | 333.09364 | 55283-68-6 | 12.59 |
| 250 | Ethiofencarb | 乙硫苯威 | C11H15NO2S | 225.08235 | 29973-13-5 | 8.74 |
| 251 | Ethiolate | 硫草敌 | C7H15NOS | 161.08744 | 2941-55-1 | 5.96 |
| 252 | Ethion | 乙硫磷 | C9H22O4P2S4 | 383.98762 | 563-12-2 | 23.98 |
| 253 | Ethofumesate | 乙氧呋草黄 | C13H18O5S | 286.08749 | 26225-79-6 | 18.17 |
| 254 | Ethoprophos | 灭线磷 | C8H19O2PS2 | 242.05641 | 13194-48-4 | 12.31 |
| 255 | Ethoxyquin | 乙氧喹啉 | C14H19NO | 217.14667 | 91-53-2 | 14.18 |
| 256 | ethychlozate | 胺草酯 | C11H11ClN2O2 | 238.05091 | 27512-72-7 | 20.29 |
| 257 | Etofenprox | 醚菊酯 | C25H28O3 | 376.20384 | 80844-07-1 | 31.92 |
| 258 | Etoxazole | 乙螨唑 | C21H23F2NO2 | 359.16969 | 153233-91-1 | 27.44 |
| 259 | Etridiazole | 土菌灵 | C5H5Cl3N2OS | 245.91882 | 2593-15-9 | 9.13 |
| 260 | Etrimfos | 乙嘧硫磷 | C10H17N2O4PS | 292.06467 | 38260-54-7 | 15.86 |
| 261 | Eugenol | 丁香酚 | C10H12O2 | 164.08373 | 97-53-0 | 7.71 |
| 262 | Famphur | 伐灭磷 | C10H16NO5PS2 | 325.02075 | 52-85-7 | 24.72 |
| 263 | Fenamidone | 咪唑菌酮 | C17H17N3OS | 311.10923 | 161326-34-7 | 27.43 |
| 264 | Fenamiphos | 苯线磷 | C13H22NO3PS | 303.1058 | 22224-92-6 | 21.87 |
| 265 | Fenarimol | 氯苯嘧啶醇 | C17H12Cl2N2O | 330.03267 | 60168-88-9 | 29.16 |
| 266 | Fenazaflor | 抗螨唑 | C15H7Cl2F3N2O2 | 373.98367 | 14255-88-0 | 24.34 |
| 267 | Fenazaquin | 喹螨醚 | C20H22N2O | 306.17321 | 120928-09-8 | 27.75 |
| 268 | Fenbuconazole | 腈苯唑 | C19H17ClN4 | 336.11417 | 114369-43-6 | 30.89 |
| 269 | Fenchlorphos | 皮蝇磷 | C8H8Cl3O3PS | 319.89973 | 299-84-3 | 17.53 |
| 270 | Fenchlorphos-Oxon | 杀螟硫磷 | C8H8Cl3O4P | 303.92258 | 3983-45-7 | 16.35 |
| 271 | Fenfuram | 甲呋酰胺 | C12H11NO2 | 201.07898 | 24691-80-3 | 15.71 |
| 272 | Fenhexamid | 环酰菌胺 | C14H17Cl2NO2 | 301.06364 | 126833-17-8 | 25.21 |
| 273 | Fenitrothion | 杀螟硫磷 | C9H12NO5PS | 277.01738 | 122-14-5 | 18.11 |
| 274 | Fenobucarb | 仲丁威 | C12H17NO2 | 207.12593 | 3766-81-2 | 11.78 |
| 275 | Fenoprop | 2,4,5-涕丙酸 | C9H7Cl3O3 | 267.94608 | 93-72-1 | 17.25 |
| 276 | Fenoprop-methyl ester | 2,4,5-涕丙酸甲酯 | C10H9Cl3O3 | 281.96173 | 4841-20-7 | 14.53 |
| 277 | Fenothiocarb | 苯硫威 | C13H19NO2S | 253.11365 | 62850-32-2 | 21.47 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 278 | Fenoxaprop-Ethyl | 噁唑禾草灵 | C18H16ClNO5 | 361.0717 | 66441-23-4 | 29.84 |
| 279 | Fenoxycarb | 苯氧威 | C17H19NO4 | 301.13141 | 72490-01-8 | 27.28 |
| 280 | Fenpiclonil | 拌种咯 | C11H6Cl2N2 | 235.9908 | 74738-17-3 | 26.41 |
| 281 | Fenpropathrin | 甲氰菊酯 | C22H23NO3 | 349.16779 | 39515-41-8 | 27.48 |
| 282 | Fenpropidin | 苯锈啶 | C19H31N | 273.24565 | 67306-00-7 | 18.04 |
| 283 | Fenpropimorph | 丁苯吗啉 | C20H33NO | 303.25621 | 67564-91-4 | 19.03 |
| 284 | Fenson | 除螨酯 | C12H9ClO3S | 267.99609 | 80-38-6 | 19.34 |
| 285 | Fensulfothion | 丰索磷 | C11H17O4PS2 | 308.03059 | 115-90-2 | 23.66 |
| 286 | Fensulfothion-oxon | 氧丰索磷 | C11H17O5PS | 292.05343 | 6552-21-2 | 22.48 |
| 287 | Fensulfothion-sulfone | 丰索磷砜 | C11H17O5PS2 | 324.0255 | 14255-72-2 | 24.21 |
| 288 | Fenthion | 倍硫磷 | C10H15O3PS2 | 278.02002 | 55-38-9 | 18.86 |
| 289 | Fenthion-oxon | 氧倍硫磷 | C10H15O4PS | 262.04287 | 6552-12-1 | 17.61 |
| 290 | Fenthion-sulfone | 倍硫磷砜 | C10H15O5PS2 | 310.00985 | 3761-42-0 | 23.8 |
| 291 | Fenthion-sulfoxide | 倍硫磷亚砜 | C10H15O4PS2 | 294.01494 | 3761-41-9 | 23.61 |
| 292 | Fentin hydroxide | 三苯基氢氧化锡 | C18H16OSn | 368.02231 | 76-87-9 | 30.86 |
| 293 | Fenuron | 非草隆 | C9H12N2O | 164.09496 | 101-42-8 | 12.27 |
| 294 | Fenvalerate | 氰戊菊酯 | C25H22ClNO3 | 419.12882 | 51630-58-1 | 32.66 |
| 295 | Ferimzone | 嘧菌腙 | C15H18N4 | 254.15315 | 89269-64-7 | 20.87 |
| 296 | Fipronil | 氟虫腈 | C12H4Cl2F6N4OS | 435.93871 | 120068-37-3 | 20.25 |
| 297 | Fipronil Desulfinyl | 溴甲腈 | C12H4Cl2F6N4 | 387.97172 | 205650-65-3 | 17.11 |
| 298 | Fipronil-sulfide | 氟虫腈亚砜 | C12H4Cl2F6N4S | 419.94379 | 120067-83-6 | 19.79 |
| 299 | Fipronil-sulfone | 氟虫腈砜 | C12H4Cl2F6N4O2S | 451.93362 | 120068-36-2 | 22.34 |
| 300 | Flamprop-isopropyl | 麦草氟异丙酯 | C19H19ClFNO3 | 363.10375 | 52756-22-6 | 23.72 |
| 301 | Flamprop-methyl | 麦草氟甲酯 | C17H15ClFNO3 | 335.07245 | 52756-25-9 | 22.56 |
| 302 | Fluacrypyrim | 嘧螨酯 | C20H21F3N2O5 | 426.14026 | 229977-93-9 | 24.39 |
| 303 | Fluazifop-butyl | 吡氟禾草灵 | C19H20F3NO4 | 383.13444 | 69806-50-4 | 23.44 |
| 304 | Fluazinam | 氟啶胺 | C13H4Cl2F6N4O4 | 463.95138 | 79622-59-6 | 24.23 |
| 305 | Flubenzimine | 嘧唑螨 | C17H10F6N4S | 416.05304 | 37893-02-0 | 22.12 |
| 306 | Fluchloralin | 氟丙草 | C12H13ClF3N3O4 | 355.05467 | 33245-39-5 | 15.33 |
| 307 | Flucythrinate | 氟氰戊菊酯 | C26H23F2NO4 | 451.15952 | 70124-77-5 | 31.73 |
| 308 | Fludioxonil | 咯菌腈 | C12H6F2N2O2 | 248.03973 | 131341-86-1 | 22.03 |
| 309 | Flufenacet | 氟噻草胺 | C14H13F4N3O2S | 363.06646 | 142459-58-3 | 19.07 |
| 310 | Flumetralin | 氟节胺 | C16H12ClF4N3O4 | 421.04525 | 62924-70-3 | 21.46 |
| 311 | Flumioxazin | 丙炔氟草胺 | C19H15FN2O4 | 354.10159 | 103361-09-7 | 32.57 |
| 312 | Fluopyram | 氟吡菌酰胺 | C16H11ClF6N2O | 396.04641 | 658066-35-4 | 20.41 |
| 313 | Fluorodifen | 消草醚 | C13H7F3N2O5 | 328.03071 | 15457-05-3 | 21.94 |
| 314 | Fluoroimide | 氟氯菌核利 | C10H4Cl2FNO2 | 258.96031 | 41205-21-4 | 13.89 |
| 315 | Fluotrimazole | 三氟苯唑 | C22H16F3N3 | 379.12963 | 31251-03-3 | 25.93 |
| 316 | Fluridone | 氟啶酮 | C19H14F3NO | 329.10275 | 59756-60-4 | 32.16 |
| 317 | Flurochloridone | 氟咯草酮 | C12H10Cl2F3NO | 311.00915 | 61213-25-0 | 19.29 |
| 318 | Fluroxypyr | 氟氯吡氧乙酸 | C7H5Cl2FN2O3 | 253.96613 | 69377-81-7 | 16.13 |
| 319 | fluroxypyr-mepthyl | 氟氯吡氧乙酸异辛酯 | C15H21Cl2FN2O3 | 366.09133 | 81406-37-3 | 25.8 |
| 320 | Flurprimidol | 呋嘧醇 | C15H15F3N2O2 | 312.10856 | 56425-91-3 | 16.92 |
| 321 | Flusilazole | 氟硅唑 | C16H15F2N3Si | 315.10033 | 85509-19-9 | 22.64 |
| 322 | Flutolanil | 氟酰胺 | C17H16F3NO2 | 323.11331 | 66332-96-5 | 22.02 |
| 323 | Flutriafol | 粉唑醇 | C16H13F2N3O | 301.10267 | 76674-21-0 | 21.7 |
| 324 | Fluxapyroxad | 氟唑菌酰胺 | C18H12F5N3O | 381.09005 | 907204-31-3 | 27.04 |
| 325 | Folpet | 灭菌丹 | C9H4Cl3NO2S | 294.90283 | 133-07-3 | 20.69 |
| 326 | Fonofos | 地虫硫磷 | C10H15OPS2 | 246.03019 | 944-22-9 | 15.09 |
| 327 | Formothion | 安果 | C6H12NO4PS2 | 256.99454 | 2540-82-1 | 16.32 |
| 328 | Fosthiazate | 噻唑磷 | C9H18NO3PS2 | 283.04657 | 98886-44-3 | 19.58 |
| 329 | Fuberidazole | 麦穗灵 | C11H8N2O | 184.06366 | 3878-19-1 | 17.22 |
| 330 | Furalaxyl | 呋霜灵 | C17H19NO4 | 301.13141 | 57646-30-7 | 20.59 |
| 331 | furametpyr | 福拉比 | C17H20ClN3O2 | 333.12441 | 123572-88-3 | 27.89 |
| 332 | Furathiocarb | 呋线威 | C18H26N2O5S | 382.15624 | 65907-30-4 | 28.02 |
| 333 | Furilazole | 解草噁唑 | C11H13Cl2NO3 | 277.02725 | 121776-33-8 | 14.24 |
| 334 | Furmecyclox | 拌种胺 | C14H21NO3 | 251.15214 | 60568-05-0 | 16.44 |
| 335 | gamma-Cyhalothrin | 氟氯氰菊酯 | C23H19ClF3NO3 | 449.10056 | 76703-62-3 | 29 |
| 336 | Griseofulvin | 灰黄霉素 | C17H17ClO6 | 352.07137 | 126-07-8 | 31.04 |
| 337 | Halfenprox | 苯螨醚 | C24H23BrF2O3 | 476.07986 | 111872-58-3 | 31.54 |
| 338 | Haloxyfop-methyl | 氟吡甲禾灵 | C16H13ClF3NO4 | 375.04852 | 69806-40-2 | 21.22 |
| 339 | alpha-HCH | 六六六 | C6H6Cl6 | 287.86007 | 319-84-6 | 13.52 |
| 340 | beta-HCH | β-六六六 | C6H6Cl6 | 287.86007 | 319-85-7 | 14.36 |
| 341 | delta-HCH | δ-六六六 | C6H6Cl6 | 287.86007 | 319-86-8 | 15.74 |
| 342 | Heptachlor | 七氯 | C10H5Cl7 | 369.8211 | 76-44-8 | 17.4 |
| 343 | Heptachlor-exo-epoxide | 环氧七氯 | C10H5Cl7O | 385.81601 | 1024-57-3 | 20.15 |
| 344 | Heptenophos | 庚烯磷 | C9H12ClO4P | 250.01617 | 23560-59-0 | 11.14 |
| 345 | Hexachlorobenzene | 六氯苯 | C6Cl6 | 281.81312 | 118-74-1 | 13.64 |
| 346 | Hexaconazole | 己唑醇 | C14H17Cl2N3O | 313.07487 | 79983-71-4 | 22 |
| 347 | Hexaflumuron | 氟铃脲 | C16H8Cl2F6N2O3 | 459.98162 | 86479-06-3 | 8.84 |
| 348 | Hexazinone | 环嗪酮 | C12H20N4O2 | 252.15863 | 51235-04-2 | 25.44 |
| 349 | Imazalil | 抑霉唑 | C14H14Cl2N2O | 296.04832 | 35554-44-0 | 21.98 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 350 | Imazamethabenz-methyl | 咪草酸 | C16H20N2O3 | 288.14739 | 81405-85-8 | 21.77 |
| 351 | Indanofan | 茚草酮 | C20H17ClO3 | 340.08662 | 133220-30-1 | 7.63 |
| 352 | Indoxacarb | 茚虫威 | C22H17ClF3N3O7 | 527.07071 | 144171-61-9 | 33.45 |
| 353 | Iodofenphos | 碘硫磷 | C8H8Cl2IO3PS | 411.83536 | 18181-70-9 | 21.9 |
| 354 | Ipconazole | 种菌唑 | C18H24ClN3O | 333.16079 | 125225-28-7 | 29.04 |
| 355 | Iprobenfos | 异稻瘟净 | C13H21O3PS | 288.0949 | 26087-47-8 | 16.12 |
| 356 | Iprodione | 异菌脲 | C13H13Cl2N3O3 | 329.0334 | 36734-19-7 | 26.8 |
| 357 | Iprovalicarb | 丙森锌 | C18H28N2O3 | 320.20999 | 140923-17-7 | 22.61 |
| 358 | Isazofos | 氯唑磷 | C9H17ClN3O3PS | 313.04168 | 42509-80-8 | 15.67 |
| 359 | Isocarbamid | 丁咪酰胺 | C8H15N3O2 | 185.11643 | 30979-48-7 | 14.81 |
| 360 | isocarbophos | 水胺硫磷 | C11H16NO4PS | 289.05377 | 24353-61-5 | 19.13 |
| 361 | Isodrin | 异艾氏剂 | C12H8Cl6 | 361.87572 | 465-73-6 | 19.73 |
| 362 | Isoeugenol | 异丁子香酚 | C10H12O2 | 164.08373 | 97-54-1 | 9.09 |
| 363 | Isofenphos | 异柳磷 | C15H24NO4PS | 345.11637 | 25311-71-1 | 20.28 |
| 364 | Isofenphos-Methyl | 甲基异柳磷 | C14H22NO4PS | 331.10072 | 99675-03-3 | 19.75 |
| 365 | Isofenphos-oxon | 氧异柳磷 | C15H24NO5P | 329.13921 | 31120-85-1 | 19.1 |
| 366 | Isomethiozin | 丁嗪草酮 | C12H20N4OS | 268.13578 | 57052-04-7 | 18.98 |
| 367 | Isoprocarb | 异丙威 | C11H15NO2 | 193.11028 | 2631-40-5 | 10.57 |
| 368 | Isopropalin | 异丙乐灵 | C15H23N3O4 | 309.16886 | 33820-53-0 | 19.77 |
| 369 | Isoprothiolane | 稻瘟灵 | C12H18O4S2 | 290.06465 | 50512-35-1 | 22.15 |
| 370 | Isoproturon | 异丙隆 | C12H18N2O | 206.14191 | 34123-59-6 | 17.47 |
| 371 | Isopyrazam | 吡唑萘菌胺 | C20H24F2N3O | 360.18874 | 881685-58-1 | 29.55 |
| 372 | Isoxadifen-ethyl | 双苯恶唑酸 | C18H17NO3 | 295.12084 | 163520-33-0 | 23.72 |
| 373 | Isoxaflutole | 异恶氯草 | C15H12F3NO4S | 359.04391 | 141112-29-0 | 21.78 |
| 374 | Isoxathion | 噁唑磷 | C13H16NO4PS | 313.05377 | 18854-01-8 | 23.11 |
| 375 | Kadethrin | 呋喃菊酯 | C23H24O4S | 396.13953 | 58769-20-3 | 35.72 |
| 376 | Kinoprene | 烯虫炔酯 | C18H28O2 | 276.20893 | 42588-37-4 | 18.96 |
| 377 | Kresoxim-methyl | 醚菌酯 | C18H19NO4 | 313.13141 | 143390-89-0 | 22.8 |
| 378 | Lactofen | 乳氟禾草灵 | C19H15ClF3NO7 | 461.04891 | 77501-63-4 | 29.08 |
| 379 | Lambda-Cyhalothrin | 高效氯氟氰菊酯 | C23H19ClF3NO3 | 449.10056 | 91465-08-6 | 29.09 |
| 380 | Lenacil | 环草啶 | C13H18N2O2 | 234.13683 | 2164-08-1 | 25.03 |
| 381 | Leptophos | 溴苯磷 | C13H10BrCl2O2PS | 409.86996 | 21609-90-5 | 28.27 |
| 382 | Lindane | 林丹 | C6H6Cl6 | 287.86007 | 58-89-9 | 14.74 |
| 383 | Linuron | 利谷隆 | C9H10Cl2N2O2 | 248.01193 | 330-55-2 | 18.27 |
| 384 | Malaoxon | 马拉氧磷 | C10H19O7PS | 314.05891 | 1634-78-2 | 17.09 |
| 385 | Malathion | 马拉硫磷 | C10H19O6PS2 | 330.03607 | 121-75-5 | 18.47 |
| 386 | Matrine | 苦参碱 | C15H24N2O | 248.18886 | 519-02-8 | 25.16 |
| 387 | Mcpa Butoxyethyl Ester | 2-甲-4-氯丁氧乙基酯 | C15H21ClO4 | 300.11284 | 19480-43-4 | 20.7 |
| 388 | MCPA-2-ETHYLHEXYL ESTER | 2甲第-2-乙基己基酯 | C17H25ClO3 | 312.14922 | 29450-45-1 | 21.48 |
| 389 | Mecarbam | 灭蚜磷 | C10H20NO5PS2 | 329.05205 | 2595-54-2 | 20.42 |
| 390 | Mecoprop | 2-甲基-4-氯丙酸 | C11H13ClO3 | 228.05532 | 7085-19-0 | 10.73 |
| 391 | Mefenacet | 苯噻酰草胺 | C16H14N2O2S | 298.0776 | 73250-68-7 | 28.65 |
| 392 | Mefenpyr-diethyl | 吡唑解草酯 | C16H18Cl2N2O4 | 372.06436 | 135590-91-9 | 26.43 |
| 393 | Mefluidide | 氟磺酰草胺 | C11H13F3N2O3S | 310.0599 | 53780-34-0 | 19.58 |
| 394 | Mepanipyrim | 嘧菌胺 | C14H13N3 | 223.11095 | 110235-47-7 | 21.66 |
| 395 | Mephosfolan | 地胺磷 | C8H16NO3PS2 | 269.03092 | 950-10-7 | 20.33 |
| 396 | Mepronil | 灭锈胺 | C17H19NO2 | 269.14158 | 55814-41-0 | 24.48 |
| 397 | Merphos | 脱叶亚磷 | C12H27PS3 | 298.10125 | 150-50-5 | 20.4 |
| 398 | Metalaxyl | 甲霜灵 | C15H21NO4 | 279.14706 | 57837-19-1 | 17.48 |
| 399 | Metamitron | 苯嗪草酮 | C10H10N4O | 202.08546 | 41394-05-2 | 22.78 |
| 400 | Metazachlor | 吡唑草胺 | C14H16ClN3O | 277.09819 | 67129-08-2 | 19.93 |
| 401 | Metconazole | 叶菌唑 | C17H22ClN3O | 319.14514 | 125116-23-6 | 27.64 |
| 402 | Methabenzthiazuron | 甲苯噻隆 | C10H11N3OS | 221.06228 | 18691-97-9 | 12.88 |
| 403 | Methacrifos | 虫螨畏 | C7H13O5PS | 240.02213 | 62610-77-9 | 9.89 |
| 404 | Methamidophos | 甲胺磷 | C2H8NO2PS | 141.00134 | 10265-92-6 | 6.21 |
| 405 | Methfuroxam | 呋菌胺 | C14H15NO2 | 229.11028 | 28730-17-8 | 19.08 |
| 406 | Methidathion | 杀扑磷 | C6H11N2O4PS3 | 301.96186 | 950-37-8 | 20.99 |
| 407 | Methiocarb | 甲硫威 | C11H15NO2S | 225.08235 | 2032-65-7 | 10.74 |
| 408 | Methiocarb-sulfoxide | 甲硫威亚砜 | C11H15NO3S | 241.07727 | 2635-10-1 | 17.13 |
| 409 | Methoprene | 烯虫丙酯 | C19H34O3 | 310.2508 | 40596-69-8 | 21.05 |
| 410 | Methoprotryne | 甲氧丹津 | C11H21N5OS | 271.14668 | 841-06-5 | 22.89 |
| 411 | Methothrin | 甲醚菊酯 | C19H26O3 | 302.18819 | 34388-29-9 | 21.87 |
| 412 | Methoxychlor | 甲氧滴滴涕 | C16H15Cl3O2 | 344.01376 | 72-43-5 | 27.33 |
| 413 | Metobromuron | 溴谷隆 | C9H11BrN2O2 | 258.00039 | 3060-89-7 | 16.36 |
| 414 | Metolachlor | 异丙甲草胺 | C15H22ClNO2 | 283.13391 | 51218-45-2 | 18.62 |
| 415 | Metolcarb | 速灭威 | C9H11NO2 | 165.07898 | 1129-41-5 | 9.31 |
| 416 | Metribuzin | 嗪草酮 | C8H14N4OS | 214.08883 | 21087-64-9 | 16.89 |
| 417 | Mevinphos | 速灭磷 | C7H13O6P | 224.04497 | 7786-34-7 | 8.69 |
| 418 | Mexacarbate | 兹克威 | C12H18N2O2 | 222.13683 | 315-18-4 | 15.75 |
| 419 | Mgk 264 | 增效胺 | C17H25NO2 | 275.18853 | 113-48-4 | 20.03 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 420 | Mirex | 火蚁灵 | C10Cl12 | 539.62623 | 2385-85-5 | 28.86 |
| 421 | Molinate | 禾草敌 | C9H17NOS | 187.10309 | 2212-67-1 | 10.67 |
| 422 | Monalide | 庚酰草胺 | C13H18ClNO | 239.10769 | 7287-36-7 | 16.33 |
| 423 | Monolinuron | 绿谷隆 | C9H11ClN2O2 | 214.05091 | 1746-81-2 | 14.42 |
| 424 | Monuron | 灭草隆 | C9H11ClN2O | 198.05599 | 150-68-5 | 16.3 |
| 425 | Musk Ambrette | 葵子麝香 | C12H16N2O5 | 268.10592 | 83-66-9 | 15.92 |
| 426 | Musk Ketone | 酮麝香 | C14H18N2O5 | 294.12157 | 81-14-1 | 18.58 |
| 427 | Musk Moskene | 麝香 | C14H18N2O4 | 278.12666 | 116-66-5 | 16.87 |
| 428 | Musk Tibetene | 西藏麝香 | C13H18N2O4 | 266.12666 | 145-39-1 | 17.74 |
| 429 | Musk Xylene | 二甲苯麝香 | C12H15N3O6 | 297.09609 | 81-15-2 | 16.41 |
| 430 | Myclobutanil | 腈菌唑 | C15H17ClN4 | 288.11417 | 88671-89-0 | 22.55 |
| 431 | Naled | 二溴磷 | C4H7Br2Cl2O4P | 377.78258 | 300-76-5 | 12.67 |
| 432 | Napropamide | 敌草胺 | C17H21NO2 | 271.15723 | 15299-99-7 | 21.83 |
| 433 | Nicotine | 烟碱 | C10H4N2 | 162.1157 | 54-11-5 | 7.72 |
| 434 | Nitralin | 甲磺乐灵 | C13H19N3O6S | 345.09946 | 4726-14-1 | 26.21 |
| 435 | Nitrapyrin | 2-氯-6-三氯甲基吡啶 | C6H3Cl4N | 228.90196 | 1929-82-4 | 9.08 |
| 436 | Nitrofen | 2,4-二氯-4'-硝基二苯醚 | C12H7Cl2NO3 | 282.9803 | 1836-75-5 | 23.21 |
| 437 | Nitrothal-Isopropyl | 酞菌酯 | C14H17NO6 | 295.10559 | 10552-74-6 | 19.38 |
| 438 | Norflurazon | 氟草敏 | C12H9ClF3N3O | 303.03862 | 27314-13-2 | 24.93 |
| 439 | Noruron | 草完隆 | C13H22N2O | 222.17321 | 18530-56-8 | 18.34 |
| 440 | Nuarimol | 氯苯嘧啶醇 | C17H12ClFN2O | 314.06222 | 63284-71-9 | 25.68 |
| 441 | Octachlorostyrene | 八氯苯乙烯 | C8Cl8 | 375.75082 | 29082-74-4 | 19.85 |
| 442 | Octhilinone | 辛噻酮 | C11H19NOS | 213.11874 | 26530-20-1 | 16.23 |
| 443 | Ofurace | 呋酰胺 | C14H16ClNO3 | 281.08187 | 58810-48-3 | 24.5 |
| 444 | Orbencarb | 坪草丹 | C12H16ClNOS | 257.06411 | 34622-58-7 | 18.1 |
| 445 | Ortho-Dichlorobenzene | 邻二氯苯 | C6H4Cl2 | 145.96901 | 95-50-1 | 4.69 |
| 446 | Oxabetrinil | 解草腈 | C12H12N2O3 | 232.08479 | 74782-23-3 | 16.17 |
| 447 | oxadiazon | 噁草酮 | C15H18Cl2N2O3 | 344.06945 | 19666-30-9 | 22.52 |
| 448 | Oxadixyl | 噁霜灵 | C14H18N2O4 | 278.12666 | 77732-09-3 | 23.83 |
| 449 | Oxycarboxin | 氧化萎锈灵 | C12H13NO4S | 267.05653 | 5259-88-1 | 26.07 |
| 450 | Oxychlordane | 氧化氯丹 | C10H4Cl8O | 419.77704 | 27304-13-8 | 20.14 |
| 451 | Oxyfluorfen | 乙氧氟草醚 | C15H11ClF3NO4 | 361.03287 | 42874-03-3 | 22.71 |
| 452 | Paclobutrazol | 多效唑 | C15H20ClN3O | 293.12949 | 76738-62-0 | 21.26 |
| 453 | Paraoxon-Ethyl | 对硫磷 | C10H14NO6P | 275.05587 | 311-45-5 | 17.64 |
| 454 | Paraoxon-Methyl | 甲基对氧磷 | C8H10NO6P | 247.02457 | 950-35-6 | 15.58 |
| 455 | parathion | 对硫磷 | C10H14NO5PS | 291.03303 | 56-38-2 | 18.96 |
| 456 | Parathion-Methyl | 甲基对硫磷 | C8H10NO5PS | 263.00173 | 298-00-0 | 17.14 |
| 457 | Pebulate | 克草敌 | C10H21NOS | 203.13439 | 1114-71-2 | 9.31 |
| 458 | Penconazole | 戊菌唑 | C13H15Cl2N3 | 283.0643 | 66246-88-6 | 20.14 |
| 459 | Pendimethalin | 胺硝草 | C13H19N3O4 | 281.13756 | 40487-42-1 | 19.92 |
| 460 | Pentachloroaniline | 五氯苯胺 | C6H2Cl5N | 262.86299 | 527-20-8 | 16.32 |
| 461 | Pentachloroanisole | 五氯苯甲醚 | C7H3Cl5O | 277.86265 | 1825-21-4 | 13.85 |
| 462 | Pentachlorobenzene | 五氯苯 | C6HCl5 | 247.85209 | 608-93-5 | 10.31 |
| 463 | Pentachlorocyanobenzene | 五氯苯甲腈 | C7Cl5N | 272.84734 | 20925-85-3 | 14.69 |
| 464 | Pentachlorophenol | 五氯酚 | C6HCl5O | 263.847 | 87-86-5 | 14.5 |
| 465 | Pentanochlor | 甲氯酰草胺 | C13H18ClNO | 239.10769 | 2307-68-8 | 18.38 |
| 466 | Pentoxazone | 环戊噁草酮 | C17H17ClFNO4 | 353.08301 | 110956-75-7 | 28.3 |
| 467 | Permethrin | 氯菊酯 | C21H20Cl2O3 | 390.07895 | 52645-53-1 | 30.25 |
| 468 | Perthane | 乙滴涕 | C18H20Cl2 | 306.09421 | 72-56-0 | 23.33 |
| 469 | Pethoxamid 烯草胺 | C16H22ClNO2 | 295.13391 | 106700-29-2 | 20.56 |
| 470 | Phenanthrene | 菲 | C14H10 | 178.07825 | 85-01-8 | 15.23 |
| 471 | Phenothrin | 苯醚菊酯 | C23H26O3 | 350.18819 | 26002-80-2 | 28.22 |
| 472 | Phenthoate | 稻丰散 | C12H17O4PS2 | 320.03059 | 2597-03-7 | 20.49 |
| 473 | Phorate | 甲拌磷 | C7H17O2PS3 | 260.01283 | 298-02-2 | 13.39 |
| 474 | Phorate-oxon-sulfone | 氧甲拌磷砜 | C7H17O5PS2 | 276.0255 | 2588-06-9 | 16.96 |
| 475 | Phorate-Sulfone | 甲拌磷砜 | C7H17O4PS3 | 292.00266 | 2588-04-7 | 18.7 |
| 476 | Phorate-Sulfoxide | 甲拌磷亚砜 | C7H17O3PS3 | 276.00774 | 2588-03-6 | 18.4 |
| 477 | Phorate-oxon | 氧甲拌磷 | C7H17O3PS2 | 244.03567 | 2600-69-3 | 11.95 |
| 478 | Phosalone | 伏杀硫磷 | C12H15ClNO4PS2 | 366.98686 | 2310-17-0 | 28.23 |
| 479 | Phosfolan | 硫环磷 | C7H14NO3PS2 | 255.01527 | 947-02-4 | 20.21 |
| 480 | Phosmet | 亚胺硫磷 | C11H12NO4PS2 | 316.99454 | 732-11-6 | 26.87 |
| 481 | Phosphamidon | 磷胺 | C10H19ClNO5P | 299.06894 | 13171-21-6 | 16.63 |
| 482 | Phthalic Acid, Bis-Butyl Ester | 邻苯二甲酸二丁酯 | C16H22O4 | 278.15181 | 84-74-2 | 18.37 |
| 483 | Phthalic Acid, Benzyl Butyl Ester | 邻苯二甲酸丁苄酯 | C19H20O4 | 312.13616 | 85-68-7 | 25.17 |
| 484 | Phthalic Acid, bis-2-ethylhexyl ester | 邻苯二甲酸二(2-乙基己)酯 | C24H38O4 | 390.27701 | 117-81-7 | 28.17 |
| 485 | Phthalic Acid, Bis-Cyclohexyl Ester | 邻苯二甲酸二环己酯 | C20H26O4 | 330.18311 | 84-61-7 | 27.83 |
| 486 | Phthalide | 四氯苯酞 | C8H2Cl4O2 | 269.88089 | 27355-22-2 | 19.19 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 487 | Phthalimide | 邻苯二甲酰亚胺 | C8H5NO2 | 147.03203 | 85-41-6 | 9.4 |
| 488 | Picolinafen | 氟吡酰草胺 | C19H12F4N2O2 | 376.08349 | 137641-05-5 | 27.22 |
| 489 | Picoxystrobin | 啶氧菌酯 | C18H16F3NO4 | 367.10314 | 117428-22-5 | 21.72 |
| 490 | Piperalin | 哌丙灵 | C16H21Cl2NO2 | 329.09493 | 3478-94-2 | 25.58 |
| 491 | Piperonyl Butoxide | 增效醚 | C19H30O5 | 338.20932 | 51-03-6 | 26.21 |
| 492 | Piperophos | 哌草磷 | C14H28NO3PS2 | 353.12482 | 24151-93-7 | 27.16 |
| 493 | Pirimicarb | 抗蚜威 | C11H18N4O2 | 238.14298 | 23103-98-2 | 16.15 |
| 494 | Pirimicarb-desmethyl | 脱甲基抗蚜威 | C10H16N4O2 | 224.12733 | 30614-22-3 | 16.5 |
| 495 | Pirimiphos-Ethyl | 乙基嘧啶磷 | C13H24N3O3PS | 333.1276 | 23505-41-1 | 19.61 |
| 496 | Pirimiphos-Methyl | 甲基嘧啶磷 | C11H20N3O3PS | 305.0963 | 29232-93-7 | 18.05 |
| 497 | Pirimiphos-methyl-N-desethyl | 甲基嘧啶磷-N-去乙基 | C9H16N3O3PS | 277.065 | 67018-59-1 | 17.44 |
| 498 | Plifenate | 二氯杀虫酯 | C10H7Cl5O2 | 333.88887 | 21757-82-4 | 17.04 |
| 499 | Prallethrin | 炔丙菊酯 | C19H24O3 | 300.17254 | 23031-36-9 | 21.06 |
| 500 | Pretilachlor | 丙草胺 | C17H26ClNO2 | 311.16521 | 51218-49-6 | 22.22 |
| 501 | Probenazole | 烯丙苯噻唑 | C10H9NO3S | 223.03031 | 27605-76-1 | 15.45 |
| 502 | Procyazine | 环丙腈津 | C10H13ClN6 | 252.08902 | 32889-48-8 | 21.13 |
| 503 | Procymidone | 腐霉利 | C13H11Cl2NO2 | 283.01668 | 32809-16-8 | 20.64 |
| 504 | Prodiamine | 氨基丙氟灵 | C13H17F3N4O4 | 350.12019 | 29091-21-2 | 18.22 |
| 505 | Profenofos | 丙溴磷 | C11H15BrClO3PS | 371.93514 | 41198-08-7 | 22.25 |
| 506 | Profluralin | 环丙氟 | C14H16F3N3O4 | 347.10929 | 26399-36-0 | 14.91 |
| 507 | Prohydrojasmon | 茉莉酮 | C15H26O3 | 254.18819 | 158474-72-7 | 15.65 |
| 508 | Promecarb | 猛杀威 | C12H17NO2 | 207.12593 | 2631-37-0 | 13.36 |
| 509 | Prometon | 扑灭通 | C10H19N5O | 225.15896 | 1610-18-0 | 14.3 |
| 510 | Prometryn | 扑草净 | C10H19N5S | 241.13612 | 7287-19-6 | 17.64 |
| 511 | Propachlor | 毒草胺 | C11H14ClNO | 211.07639 | 1918-16-7 | 11.82 |
| 512 | Propamocarb | 霜霉威 | C9H20N2O2 | 188.15248 | 24579-73-5 | 8.24 |
| 513 | Propanil | 敌稗 | C9H9Cl2NO | 217.00612 | 709-98-8 | 16.77 |
| 514 | Propaphos | 丙虫磷 | C13H21O4PS | 304.08982 | 7292-16-2 | 21.17 |
| 515 | Propargite | 炔螨特 | C19H26O4S | 350.15518 | 2312-35-8 | 25.96 |
| 516 | Propazine | 扑灭津 | C9H16ClN5 | 229.10942 | 139-40-2 | 14.59 |
| 517 | Propetamphos | 异丙氧磷 | C10H20NO4PS | 281.08507 | 31218-83-4 | 14.99 |
| 518 | Propham | 苯胺灵 | C10H13NO2 | 179.09463 | 122-42-9 | 9.24 |
| 519 | Propiconazole | 丙环唑 | C15H17Cl2N3O2 | 341.06978 | 60207-90-1 | 25 |
| 520 | Propisochlor | 异丙草胺 | C15H22ClNO2 | 283.13391 | 86763-47-5 | 17.4 |
| 521 | Propoxur | 残杀威 | C11H15NO3 | 209.10519 | 114-26-1 | 11.77 |
| 522 | Propylene Thiourea | 丙烯硫脲 | C4H8N2S | 116.04082 | 2122-19-2 | 10.83 |
| 523 | Propyzamide | 炔苯酰草胺 | C12H11Cl2NO | 255.02177 | 23950-58-5 | 15.13 |
| 524 | Prosulfocarb | 苄草丹 | C14H21NOS | 251.13439 | 52888-80-9 | 17.88 |
| 525 | Prothioconazole-desthio | 脱硫丙硫菌唑 | C14H15Cl2N3O | 311.05922 | 120983-64-4 | 22.9 |
| 526 | Prothiofos | 丙硫磷 | C11H15Cl2O2PS2 | 343.96281 | 34643-46-4 | 22.08 |
| 527 | Pyracarbolid | 吡酰灵 | C13H15NO2 | 217.11028 | 24691-76-7 | 19.54 |
| 528 | Pyraclostrobin | 百克敏 | C19H18ClN3O4 | 387.09858 | 175013-18-0 | 32.75 |
| 529 | Pyrazophos | 吡菌磷 | C14H20N3O5PS | 373.08613 | 13457-18-6 | 29.28 |
| 530 | Pyrethrin I | 除虫菊素 I | C21H28O3 | 328.20384 | 121-21-1 | 24.7 |
| 531 | Pyrethrin II | 除虫菊素 II | C22H28O5 | 372.19367 | 121-29-9 | 29.49 |
| 532 | Pyributicarb | 稻草丹 | C18H22N2O2S | 330.1402 | 88678-67-5 | 26.55 |
| 533 | Pyridaben | 哒螨灵 | C19H25ClN2OS | 364.13761 | 96489-71-3 | 30.44 |
| 534 | Pyridalyl | 三氟甲吡醚 | C18H14Cl4F3NO3 | 488.96799 | 179101-81-6 | 32 |
| 535 | Pyridaphenthion | 哒嗪硫磷 | C14H17N2O4PS | 340.06467 | 119-12-0 | 26.73 |
| 536 | Pyrifenox | 啶斑肟 | C14H12Cl2N2O | 294.03267 | 88283-41-4 | 21.23 |
| 537 | Pyriftalid | 环酯草醚 | C15H14N2O4S | 318.06743 | 135186-78-6 | 29.27 |
| 538 | Pyrimethanil | 嘧霉胺 | C12H13N3 | 199.11095 | 53112-28-0 | 15.36 |
| 539 | Pyriproxyfen | 吡丙醚 | C20H19NO3 | 321.13649 | 95737-68-1 | 28.6 |
| 540 | Pyroquilon | 咯喹酮 | C11H11NO | 173.08406 | 57369-32-1 | 15.08 |
| 541 | Quinalphos | 喹硫磷 | C12H15N2O3PS | 298.0541 | 13593-03-8 | 20.51 |
| 542 | Quinoclamine | 灭藻醌 | C10H6ClNO2 | 207.00871 | 2797-51-5 | 18.36 |
| 543 | Quinoxyfen | 苯氧喹啉 | C15H8Cl2FNO | 306.9967 | 124495-18-7 | 25.04 |
| 544 | Quintozene | 五氯硝基苯 | C6Cl5NO2 | 292.83717 | 82-68-8 | 14.54 |
| 545 | Quizalofop-Ethyl | 喹禾灵 | C19H17ClN2O4 | 372.08769 | 76578-14-8 | 31.71 |
| 546 | Rabenzazole | 吡咪唑 | C12H12N4 | 212.1062 | 40341-04-6 | 19.1 |
| 547 | Resmethrin | 苄呋菊酯 | C22H26O3 | 338.18819 | 10453-86-8 | 26.3 |
| 548 | S 421 | 八氯二丙醚 | C6H6Cl8O | 373.79269 | 127-90-2 | 17.82 |
| 549 | Schradan | 八甲磷 | C8H24N4O3P2 | 286.13236 | 152-16-9 | 14.05 |
| 550 | Sebuthylazine | 仲丁津 | C9H16ClN5 | 229.10942 | 7286-69-3 | 16.13 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 551 | Sebuthylazine-desethyl | 去乙基灭丁津 | C7H12ClN5 | 201.07812 | 37019-18-4 | 14.44 |
| 552 | Secbumeton | 密草通 | C10H19N5O | 225.15896 | 26259-45-0 | 15.72 |
| 553 | Siduron | 环草隆 | C14H20N2O | 232.15756 | 1982-49-6 | 21.91 |
| 554 | Silafluofen | 白蚁灵 | C25H29FO2Si | 408.19209 | 105024-66-6 | 32.11 |
| 555 | Silthiofam | 硅噻菌胺 | C13H21NOSSi | 267.11131 | 175217-20-6 | 16.33 |
| 556 | Simazine | 西玛津 | C7H12ClN5 | 201.07812 | 122-34-9 | 14.29 |
| 557 | Simeconazole | 氟硅唑 | C14H20FN3OSi | 293.13597 | 149508-90-7 | 17.2 |
| 558 | Simeton | 西玛通 | C8H15N5O | 197.12766 | 673-04-1 | 13.82 |
| 559 | Simetryn | 西草净 | C8H15N5S | 213.10482 | 1014-70-6 | 17.33 |
| 560 | Spirodiclofen | 螺螨酯 | C21H24Cl2O4 | 410.10517 | 148477-71-8 | 30.01 |
| 561 | Spiromesifen | 螺甲螨酯 | C23H30O4 | 370.21441 | 283594-90-1 | 26.48 |
| 562 | Spirotetramat-mono-hydroxy | 螺虫乙酯_单_羟基 | C18H25NO3 | 303.18344 | 1172134-12-1 | 29.99 |
| 563 | Spiroxamine | 螺环菌胺 | C18H35NO2 | 297.26678 | 118134-30-8 | 17.22 |
| 564 | Sulfallate | 莠草双 | C8H14ClNS2 | 223.02562 | 95-06-7 | 13.53 |
| 565 | Sulfotep | 治螟磷 | C8H20O5P2S2 | 322.02274 | 3689-24-5 | 13.04 |
| 566 | Sulprofos | 硫丙磷 | C12H19O2PS3 | 322.02848 | 35400-43-2 | 24.54 |
| 567 | Tau-Fluvalinate | 氟胺氰菊酯 | C26H22ClF3N2O3 | 502.12711 | 102851-06-9 | 32.87 |
| 568 | TCMTB | 苯并噻唑 | C9H6N2S3 | 237.96931 | 21564-17-0 | 21.82 |
| 569 | Tebuconazole | 戊唑醇 | C16H22ClN3O | 307.14514 | 107534-96-3 | 25.76 |
| 570 | Tebufenpyrad | 吡螨胺 | C18H24ClN3O | 333.16079 | 119168-77-3 | 27.66 |
| 571 | Tebupirimfos | 丁基嘧啶磷 | C13H23N2O3PS | 318.1167 | 96182-53-5 | 16.13 |
| 572 | Tebutam | 牧草胺 | C15H23NO | 233.17796 | 35256-85-0 | 13.27 |
| 573 | Tebuthiuron | 丁噻隆 | C9H16N4OS | 228.10448 | 34014-18-1 | 10.25 |
| 574 | Tecnazene | 四氯硝基苯 | C6HCl4NO2 | 258.87614 | 117-18-0 | 11.54 |
| 575 | Teflubenzuron | 氟苯脲 | C14H6Cl2F4N2O2 | 379.97425 | 83121-18-0 | 8.03 |
| 576 | Tefluthrin | 七氟菊酯 | C17H14ClF7O2 | 418.05706 | 79538-32-2 | 15.88 |
| 577 | Temephos | 双硫磷 | C16H20O6P2S3 | 465.98973 | 3383-96-8 | 36.08 |
| 578 | Tepraloxydim | 吡喃草酮 | C17H24ClNO4 | 341.13939 | 149979-41-9 | 24.93 |
| 579 | Terbacil | 特草定 | C9H13ClN2O2 | 216.06656 | 5902-51-2 | 15.6 |
| 580 | Terbucarb | 特草灵 | C17H27NO2 | 277.20418 | 1918-11-2 | 16.89 |
| 581 | Terbufos | 特丁硫磷 | C9H21O2PS3 | 288.04413 | 13071-79-9 | 14.97 |
| 582 | Terbufos-Sulfone | 特丁硫磷砜 | C9H21O4PS3 | 320.03396 | 56070-16-7 | 20.11 |
| 583 | Terbumeton | 特丁通 | C10H19N5O | 225.15896 | 33693-04-8 | 14.69 |
| 584 | Terbuthylazine | 特丁津 | C9H16ClN5 | 229.10942 | 5915-41-3 | 14.97 |
| 585 | Terbutryn | 特丁净 | C10H19N5S | 241.13612 | 886-50-0 | 18.08 |
| 586 | tert-butyl-4-Hydroxyanisole | 叔丁基_4_羟基苯甲醚 | C11H16O2 | 180.11503 | 25013-16-5 | 9.67 |
| 587 | Tetrachlorvinphos | 杀虫畏 | C10H9Cl4O4P | 363.89926 | 22248-79-9 | 21.3 |
| 588 | Tetraconazole | 氟醚唑 | C13H11Cl2F4N3O | 371.02153 | 112281-77-3 | 19.14 |
| 589 | Tetradifon | 三氯杀螨砜 | C12H6O4Cl2S | 353.88426 | 116-29-0 | 28.03 |
| 590 | Tetramethrin | 胺菊酯 | C19H25NO4 | 331.17836 | 7696-12-0 | 27.24 |
| 591 | Tetrasul | 杀螨好 | C12H6Cl4S | 321.89443 | 2227-13-6 | 24.38 |
| 592 | Thenylchlor | 噻吩草胺 | C16H18ClNO2S | 323.07468 | 96491-05-3 | 25.59 |
| 593 | Thiabendazole | 噻菌灵 | C10H7N3S | 201.03607 | 148-79-8 | 20.39 |
| 594 | Thiazafluron | 噻氟隆 | C6H7F3N4OS | 240.02927 | 25366-23-8 | 6.44 |
| 595 | Thiazopyr | 噻唑烟酸 | C16H17F5N2O2S | 396.09309 | 117718-60-2 | 18.59 |
| 596 | Thiobencarb | 杀草丹 | C12H16ClNOS | 257.06411 | 28249-77-6 | 18.71 |
| 597 | Thiocyclam | 杀虫环 | C5H11NS3 | 181.00536 | 31895-21-3 | 10.02 |
| 598 | Thiofanox | 久效威 | C9H18N2O2S | 218.1089 | 39196-18-4 | 6.76 |
| 599 | Thiometon | 甲基乙拌磷 | C6H15P2S3 | 245.99718 | 640-15-3 | 13.8 |
| 600 | Thionazin | 虫线磷 | C8H13N2O3PS | 248.03845 | 297-97-2 | 11.72 |
| 601 | Tiocarbazil | 仲草丹 | C16H25NOS | 279.16569 | 36756-79-3 | 19.34 |
| 602 | Tolclofos-Methyl | 甲基立枯磷 | C9H11Cl2O3PS | 299.95436 | 57018-04-9 | 17.19 |
| 603 | Tolfenpyrad | 唑虫酰胺 | C21H22ClN3O2 | 383.14006 | 129558-76-5 | 34.17 |
| 604 | Tolylfluanid | 对甲抑菌灵 | C10H13Cl2FN2O2S2 | 345.97795 | 731-27-1 | 20.25 |
| 605 | Tralkoxydim | 三甲苯草酮 | C20H27NO3 | 329.19909 | 87820-88-0 | 28.77 |
| 606 | Trans-Chlordane | 反式氯丹 | C10H6Cl8 | 405.79777 | 5103-74-2 | 21.04 |
| 607 | Trans-Nonachlor | 反式九氯 | C10H5Cl9 | 439.7588 | 39765-80-5 | 21.61 |
| 608 | Trans-Permethrin | 反式氯菊酯 | C21H20Cl2O3 | 390.07895 | 61949-77-7 | 30.45 |
| 609 | Transfluthrin | 四氟苯菊酯 | C15H12Cl2F4O2 | 370.01505 | 118712-89-3 | 17.49 |
| 610 | triallate | 野麦畏 | C10H16Cl3NOS | 303.00182 | 2303-17-5 | 15.88 |
| 611 | Triadimefon | 三唑酮 | C14H16ClN3O2 | 293.09311 | 43121-43-3 | 19.09 |
| 612 | Triadimenol | 三唑醇 | C14H18ClN3O2 | 295.10876 | 55219-65-3 | 20.93 |
| 613 | Triamiphos | 威菌磷 | C12H19N6OP | 294.1358 | 1031-47-6 | 24 |
| 614 | Triapenthenol | 抑芽唑 | C15H25N3O | 263.19926 | 76608-88-3 | 18.39 |
| 615 | Triazophos | 三唑磷 | C12H16N3O3PS | 313.065 | 24017-47-8 | 24.49 |
| 616 | Tribufos | 脱叶磷 | C12H27OPS3 | 314.09617 | 78-48-8 | 22.56 |
| 617 | Tributyl Phosphate | 三正丁基磷酸盐 | C12H27O4P | 266.1647 | 126-73-8 | 12.42 |
| 618 | Trichloronat | 坏虫磷 | C10H12Cl3O2PS | 331.93612 | 327-98-0 | 19.28 |
| 619 | Triclopyr | 绿草定 | C7H4Cl3NO3 | 254.92568 | 55335-06-3 | 15.61 |

TABLE 2-continued

List of over 600 pesticides determined by GC-Q-Orbitrap

| NO. | Compound Name | Chinese name | Compound Formula | Exactive Mass | Cas Number | Retention Time (min) |
|---|---|---|---|---|---|---|
| 620 | Tricyclazole | 三环唑 | C9H7N3S | 189.03607 | 41814-78-2 | 22.03 |
| 621 | Tridiphane | 伏草环 | C10H7Cl5O | 317.89395 | 58138-08-2 | 17.6 |
| 622 | Trietazine | 草达津 | C9H16ClN5 | 229.10942 | 1912-26-1 | 14.92 |
| 623 | Trifenmorph | 杀螺吗啉 | C23H23NO | 329.17797 | 1420-06-0 | 29.03 |
| 624 | Trifloxystrobin | 肟菌酯 | C20H19F3N2O4 | 408.12969 | 141517-21-7 | 25.13 |
| 625 | Trifluralin | 氟乐灵 | C13H16F3N3O4 | 335.10929 | 1582-09-8 | 12.95 |
| 626 | Trinexapac-Ethyl | 抗倒酯 | C13H16O5 | 252.09977 | 95266-40-3 | 18.09 |
| 627 | Triphenyl phosphate | 磷酸三苯酯 | C18H15O4P | 326.0708 | 115-86-6 | 25.94 |
| 628 | Uniconazole | 烯效唑 | C15H18ClN3O | 291.11384 | 83657-22-1 | 22.39 |
| 629 | Vernolate | 灭草猛 | C10H21NOS | 203.13439 | 1929-77-7 | 9.08 |
| 630 | Vinclozolin | 乙烯菌核利 | C12H9Cl2NO3 | 284.99595 | 50471-44-8 | 17.1 |
| 631 | Xmc(3,5-Xylyl Methylcarbamate) | 灭除威 | C10H13NO2 | 179.09463 | 2655-14-3 | 10.94 |
| 632 | Zoxamide | 苯酰菌胺 | C14H16Cl3NO2 | 335.02466 | 156052-68-5 | 26.35 |

Figure 6:
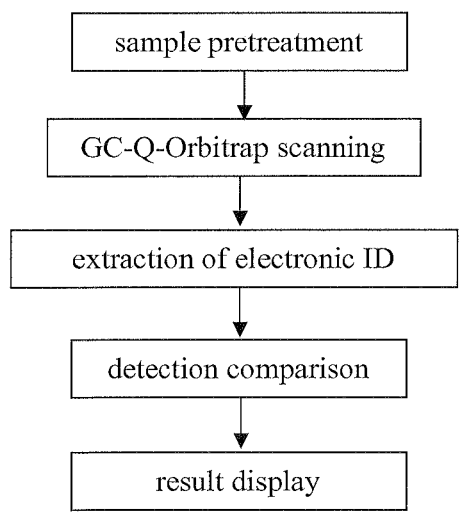
FIG. 6 shows pesticide residue detection method procedure.

FIG. 6 shows the pesticide residues detection electronic method proposed by the present invention. Through one sample preparation, over 600 pesticides could be screened by GC-Q-Orbitrap technique without using pesticide standards as references and qualitatively identified by the electronic standards, thus achieving the replacement of the pesticide material standards with electronic ID, meantime realizing the milestone development from target detection to non-target screening. It saves the resources, reduces the contamination, increases analysis speed, and meets the requirement of green development, environmental friendliness, clean and efficiency.

Example 1

Example of screening and confirmation techniques for over 600 pesticide (described in Table 2) residues in head cabbage by GC-Q-Orbitrap, the detail steps are:

1. Sample Pretreatment Procedure:

1.1 the edible portion of the head cabbage sample is chopped, blended, sealed, and labeled;

1.2 weigh 10.0 g (accurate to 0.01 g) of head cabbage sample to 100 mL centrifuge tube, add 40 mL of 1% acetonitrile acetic acid, and the mixture is then blended by homogenizer at 10 000 rpm for 1 minute. Add 1 g of sodium chloride and 4 g of anhydrous magnesium sulfate, the centrifuge tube is shaken for 10 minutes, and then centrifuged at 4200 rpm for 5 minutes, take 20 mL of supernatants into 150 mL pear-shape bottle, and evaporate to 1 mL on a rotary evaporator at 40° C. water bath for clean-up.

1.3 CarbonNH2 column is used, add about 2 cm anhydrous sodium sulfate into Carbon/NH2 column, wash the SPE column with 5 mL acetonitrile+toluene (3+1, v/v) and discard the effluents, when the liquid surface reaching the top of sodium sulfate, transfer the sample concentrate into SEP column and put a 50 mL pear-shaped bottle below it to receive them, wash the sample bottle 3 times with 2 mL acetonitrile+toluene each time and transfer the cleansing fluid into SPE column. A 50 mL reservoir was connected to the column, the pesticide and its corresponding chemicals are eluted with 25 mL acetonitrile+toluene, merged in the pear-shape bottle and evaporated to 0.5 mL on a rotary evaporator at 40° C. water bath.

1.4 The concentrate is dried under nitrogen, made up to volume with 1 mL of ethyl acetate, and filtered through a 0.22 μm filter membrane for GC-Q-Orbitrap detection.

2. GC-Q-Orbitrap Operation Conditions

Chromatographic conditions: gas chromatographic column is TG-5SILMS, 30 m×0.25 mm (i.d.)×0.25 μm mass spectrum special column; programmed temperature process: 40° C., kept for 1 minute; raised to 130° C. at 30° C./minute; raised to 250° C. at 5° C./minute; raised to 300° C. at 10° C./minute, and kept for 5 minute; carrier gas: helium, purity 99.999%; flow rate: 1.2 mL/minute; injection port type: PTV; injection volume: 1 μL; injection mode: temperature programmed injection, splitless time 1.5 minutes.

Mass spectrometry condition: EI source voltage: 70 eV; ion source temperature: 230° C.; transmission line temperature: 280° C.; solvent delay: 4 min; scan mode: full MS; mass scan range: 50-600 m/z; resolution: 60,000 FHWM (200 m/z); heptachlor epoxide is used to adjust retention time. The mass spectrometry results are collected and processed by TraceFinder (Version. 4.0); the chromatograms and mass spectrum of the head cabbage under the specified chromatographic mass spectrometry conditions are obtained, and all retention times in the chromatogram and their corresponding accurate mass numbers are extracted and the electronic ID of the pesticide in the head cabbage corresponding to all retention times is established.

3. Pesticide Residues in Cabbage Sample Screening

The sample solution is tested under Full MS mode, the screening result is compared with GC-Q-Orbitrap electronic ID database to get the pesticide residues screening result. The electronic ID of head cabbage is sequentially compared with each pesticide compound electronic ID in electronic ID database. If (ΔT≤0.15 and ΔP≤10%), then record this pesticide compound; if (ΔT 0.15 and 10%<ΔP≤30%), judge whether this pesticide compound is included by the comparison of height and overlap ratio of the mass spectrum peak in the mass spectrum, otherwise it will be compared with the next electronic ID of the pesticide in the cabbage; when the detection is completed, information of the pesticide compounds contained in the head cabbage sample solution is displayed.

GC-Q-Orbitrap screening results in head cabbage samples from a provincial capital.

12 head cabbage samples sold in a provincial capital are collected, and over 600 pesticide residues are screened by GC-Q-Orbitrap. 12 pesticide residues are detected by GC-Q-Orbitrap technique in total 32 times frequency in these 12 samples. The results are shown in Table 3.

TABLE 3

GC-Q-Orbitrap screening results in cabbage samples from a provincial capital

| No. | Pesticide | Frequency |
| --- | --- | --- |
| 1 | Propiconazole | 7 |
| 2 | Azoxystrobin | 4 |
| 3 | Pyrimethanil | 4 |
| 4 | Cyromazine | 4 |
| 5 | Metalaxyl | 3 |
| 6 | Profenofos | 2 |
| 7 | Oxadixyl | 2 |
| 8 | Malathion | 2 |
| 9 | Chlorfenapyr | 1 |
| 10 | Picoxystrobin | 1 |
| 11 | Methamidophos | 1 |
| 12 | Myclobutanil | 1 |
| Total | | 32 |

Example 2

Example of GC-Q-Orbitrap screening and confirmation techniques for over 600 pesticide residues (described in Table 2) in tomatoes.

The sample pretreatment, GC-Q-Orbitrap operation conditions and pesticide residues screening process refer to Example 1.

GC-Q-Orbitrap screening results of tomato samples from a provincial capital.

16 tomato samples sold in a provincial capital are collected, and over 600 pesticide residues are screened by GC-Q-Orbitrap. 16 pesticide residues are detected by GC-Q-Orbitrap technique in total 45 times frequency in above 15 samples. The results are shown in Table 4.

TABLE 4

GC-Q-Orbitrap screening results in tomato samples from a provincial capital

| No. | Pesticide | Frequency |
| --- | --- | --- |
| 1 | Propiconazole | 7 |
| 2 | Carbofuran | 6 |
| 3 | Dimethomorph | 5 |
| 4 | Azoxystrobin | 4 |
| 5 | Pyrimethanil | 4 |
| 6 | Cyromazine | 2 |
| 7 | Metalaxyl | 3 |
| 8 | Profenofos | 3 |
| 9 | Oxadixyl | 2 |
| 10 | Malathion | 2 |
| 11 | Tebuconazole | 2 |
| 12 | Diniconazole | 1 |
| 13 | Chlorfenapyr | 1 |
| 14 | Picoxystrobin | 1 |
| 15 | Methamidophos | 1 |
| 16 | Myclobutanil | 1 |
| Total | | 45 |

Example 3

Example of GC-Q-Orbitrap screening and confirmation techniques for over 600 pesticide residues (described in Table 2) in grapes.

The sample pretreatment, GC-Q-Orbitrap operation conditions and pesticide residues screening process refer to Example 1.

16 grape samples sold in a provincial capital are collected, and over 600 pesticide residues are screened by GC-Q-Orbitrap. 21 pesticide residues are detected by GC-Q-Orbitrap technique in total 73 times frequency in above 16 samples. The results are shown in Table 5.

TABLE 5

GC-Q-Orbitrap screening results in grape samples from a provincial capital

| No. | Pesticide | Frequency |
| --- | --- | --- |
| 1 | Dimethomorph | 10 |
| 2 | Tebuconazole | 9 |
| 3 | Boscalid | 7 |
| 4 | Pyrimethanil | 6 |
| 5 | Azoxystrobin | 5 |
| 6 | Propamocarb | 5 |
| 7 | Difenoconazole | 4 |
| 8 | Myclobutanil | 4 |
| 9 | Hexaconazole | 3 |
| 10 | Picoxystrobin | 3 |
| 11 | Procymidone | 3 |
| 12 | Cyprodinil | 2 |
| 13 | Oxadixyl | 2 |
| 14 | Fluopyram | 2 |
| 15 | Metalaxyl | 2 |
| 16 | Fenbuconazole | 1 |
| 17 | Trifloxystrobin | 1 |
| 18 | Chlorpyrifos | 1 |
| 19 | Flusilazole | 1 |
| 20 | Fenhexamid | 1 |
| 21 | Fenpropathrin | 1 |
| Total | | 73 |

The above detailed description is provided only to specifically describe some feasible embodiments of the present invention rather than limit the protection scope of the present invention. Any equivalent embodiment or modification implemented without departing from the spirit of the present invention shall be deemed as falling into the protection scope of the present invention.

The invention claimed is:

1. An electronic ID database of pesticide compounds in edible agro-products based on GC-Q-Orbitrap comprising various pesticide compounds electronic ID, which comprises pesticide compound information, retention time, mass spectrum, and fragment ions information, wherein:
the pesticide compound information comprises compound name and its molecular formula;
preparing pesticide samples, the chromatogram of the pesticide compound under the specific chromatography mass spectrometry condition is obtained by GC-Q-Orbitrap under Full MS mode, wherein the peak time in the chromatogram is the retention time;
the mass spectrum is the first level full scan spectrum at the retention time by GC-Q-Orbitrap instrument;
fragment ions are selected by their mass spectrum, and comprise one base peak ion and multiple confirmation ions, a base peak ion is a fragment ion with highest abundance and the largest mass number; with the proviso that the base peak ion cannot be the isotopic peak ion;
the fragment ion information comprises ion abundance ratio and theoretical accurate mass number;
the ion abundance ratio is a signal strength ratio between the fragment ion and the base peak ion;
the database is sorted according to the retention time.

2. The electronic ID database according to claim 1, wherein the database comprises an intelligent matching model, the matching model in the electronic ID adds an intelligent matching value $P_m$, and the calculation model is:

$$P_m = W_b M_b + W_q \cdot \sum_{i=1}^{n-2}(M_i \cdot W_i);$$

$$W_i = \frac{I_i - I_{i+1}}{I_1 - I_{n-1}};$$

$$W_b + W_q = 1;$$

wherein $M_b$ is a theoretical accurate mass number of base peak ion, $M_i$ is an accurate mass number of the ith confirmation ion, $W_i$ is a weight of the ith confirmation ion, $I_i$ is an ion abundance ratio of ith confirmation ion, a confirmation ions order is descending according to the abundance ratio, $W_b$ is the weight of the base peak ion, $W_q$ is the complex weight of confirmation ions, and n is the number of fragment ions.

3. The electronic ID database of pesticide compounds according to claim 1, wherein the values of $W_b$ and $W_q$ are adjusted according to intelligent matching model, generally $W_b = W_q = 0.5$.

4. The electronic ID database according to claim 1, wherein the fragment ion is selected according to ion abundance and ion mass number, an ion abundance is the ion signal strength in the mass spectrum, the number of fragment ions is 5, the rule of the fragment ion selection is:

if $\Delta I > 10\%$, select a maximum value from $I_i$ and $I_j$; otherwise, select a maximum value from $M_i$ and $M_j$;

wherein: $I_i$ and $I_j$ are abundance ratios of the two nearest fragment ions, $\Delta I = |I_i - I_j|$, $M_i$ and $M_j$ are an accurate mass number of the above two fragment ions, and the fragment ion order is descending according to the abundance ratio.

5. The electronic ID database of pesticide compounds according to claim 1, wherein the confirmation method of fragment ions theoretical accurate mass number is:

1) according to the compound molecular formula, an element composition of fragment ion is identified;
2) according to the mass number M of the fragment ion, a possible element composition list of the fragment ion is calculated as;

$$M = \sum_{i=1}^{n} M_i y_i$$

wherein, $M_i$ is an accurate mass number of the ith fragment ion, n is a number of fragment ions element, and $y_i$ is a number of the corresponding element in the ith fragment ion, 3) through molecular structure cracking mechanism, selecting a reasonable fragment ion element composition from a list of fragment ion element composition, and the theoretical accurate mass number M' is calculated as follows $$M' = M_1 y'_1 + M_2 y'_2 + \ldots + M_n y'_n,$$

wherein, $M_1, M_2 \ldots M_n$ are the accurate mass numbers of the fragment ion elements, and $y'_1, y'_2 \ldots y'_n$ are the numbers of the corresponding elements of preferred fragment ion element composition.

6. The electronic ID database according to claim 1, wherein the pesticide compound retention index is calculated when 2 or more peaks appear in the chromatography, pesticide compound retention time is determined by a similarity between the retention index and standard retention index of the pesticide compound;

a calculation method of retention index $R_I$ is:

$$R_I = 100Z + \frac{100[\log t_R(x) - t'_R(z)]}{\log t_R(z+1) - \log t_R(z)}$$

wherein, $t_R$ is the calibrated retention time, and z, z+1 are the carbon numbers of n-alkane eluted before and after the pesticide compound (x) elution respectively, $t_R(z) < t_R(x) < t_R(z+1)$, generally the carbon number of n-alkane z is greater than 4.

7. The electronic ID database according to claim 1, wherein the chromatography mass spectrometry conditions are:

chromatography conditions: gas chromatographic column is TG-5SILMS, 30 m×0.25 mm (i.d.)×0.25 μm mass spectrometry special column; programmed temperature process: 40° C., kept for 1 minute; raised to 130° C. at 30° C./minute; raised to 250° C. at 5° C./minute; raised to 300° C. at 10° C./minute, and kept for 5 minutes; carrier gas: helium, purity ≥99.999%; flow rate: 1.2 mL/minute; injection port type: PTV; injection volume: 1 μL; and injection mode: temperature programmed injection, splitless time 1.5 minutes; and mass spectrometry conditions: EI source voltage: 70 eV; ion source temperature: 230° C.; transmission line temperature: 280° C.; solvent delay: 4 minutes; scan mode: Full MS; mass scan range: 50-600 m/z; resolution: 60,000 FHWM (200 m/z); and heptachlor epoxide is used to adjust retention time.

8. A method for detection of pesticide compounds comprising:

1) sample to be tested is homogenized and extracted with acetonitrile acetic acid and mixture is dehydrated, centrifuged, concentrated, and then purified by Carbon/NH2 column, and residual pesticide is eluted by acetonitrile+toluene, and concentrated and filtered to prepare a sample solution to be tested;
2) a chromatography and mass spectrum of the tested solution are obtained under specific chromatography and mass spectrometry conditions by GC-Q-Orbitrap under Full MS mode;
3) all retention time and corresponding accurate mass number are extracted, establish an electronic ID for all unknown compounds corresponding to the retention time;
4) an unknown electronic ID is sequentially compared with each pesticide compound electronic ID in the electronic ID database; if $\Delta T \leq 0.15$ and $\Delta P \leq 10\%$, the pesticide compound is recorded, otherwise it is compared with the next unknown electronic ID; and 5) after detection is completed, information of the pesticide compound contained in the test sample solution is displayed;

wherein, ΔT is the difference between the retention time of unknown and that of any pesticide compound in the database;

$$\Delta P = \frac{|P_c - P_i|}{\min(P_c, P_i)}$$

wherein, $P_c$ is the intelligent matching value of the unknown, $P_i$ is the intelligent matching value of the any pesticide compound in the database.

9. The method for detection of pesticide compounds according to claim 8, wherein, in step 4 if ΔT≤0.15 and 10%<ΔP≤30%, whether the pesticide is comprised or not is judged by a comparison of height and overlap ratio of the mass spectrum peak.

10. The method for detection of pesticide compounds in edible according to claim 8, wherein, in step 1 the sample pretreatment is as follows:

weigh 10.0 g to an accuracy of 0.01 g of sample to 100 mL centrifuge tube, add 30-40 mL acidified acetonitrile, homogenize at 10,000-11,000 rpm for 1-2 minutes, add anhydrous magnesium sulfate and sodium chloride (mass ratio 4/1), the centrifuge tube is shaken for 8-10 minutes, and then centrifuged at 4200 rpm for 5-7 minutes, take 15-20 mL of supernatants into 150 mL pear-shape bottle, and evaporate to 1-2 mL on a rotary evaporator at 40° C. water bath for clean-up, using a CarbonNH2 column, add 1-2 cm anhydrous sodium sulfate to the CarbonNH$_2$ column, SPE purification column is prewashed with 5-6 mL acetonitrile/toluene solution, tap purification column gently to remove bubble, discard effluent under the purification column, when the liquid level is slightly above the top of sodium sulfate, transfer the concentrate to the purification column with a 50 mL pear-shape bottle under it, the pear-shape bottle is rinsed with 2-3 mL acetonitrile/toluene solution, and cleaning solution is decanted to the purification column, repeat 2 to 3 times, the column is connected with a 25 mL reservoir and eluted with 25-30 mL acetonitrile-toluene solution; the entire volume of effluent is collected and concentrated to 0.5 mL and then evaporated to dryness by a nitrogen, after adding 1 mL of ethyl acetate solution, it is dissolved by sonication and filtered through a 0.22 μm nylon membrane.

11. The electronic ID database according to claim 2, wherein the confirmation method of fragment ions theoretical accurate mass number is:

1) according to the compound molecular formula, an element composition of fragment ion is identified;

2) according to the mass number M of the fragment ion, a possible element composition list of the fragment ion is calculated as;

$$M = \sum_{i=1}^{n} M_i y_i$$

wherein, $M_i$ is an accurate mass number of the ith fragment ion, n is a number of fragment ions element, and $y_i$ is a number of the corresponding element in the ith fragment ion, 3) through molecular structure cracking mechanism, selecting a reasonable fragment ion element composition from a list of fragment ion element composition, and the theoretical accurate mass number M' is calculated as follows $$M' = M_1 y'_1 + M_2 y'_2 + \ldots + M_n y'_n$$

wherein, $M_1, M_2 \ldots M_n$ are the accurate mass numbers of the fragment ion elements, and $y'_1, y'_2 \ldots y'_n$ are the numbers of the corresponding elements of preferred fragment ion element composition.

12. The electronic ID database according to claim 2, wherein the pesticide compound retention index is calculated when 2 or more peaks appear in the chromatography, pesticide compound retention time is determined by a similarity between the retention index and standard retention index of the pesticide compound;

a calculation method of retention index $R_I$ is:

$$R_I = 100Z + \frac{100[\log t_R(x) - t'_R(z)]}{\log t_R(z+1) - \log t_R(z)}$$

wherein, $t_R$ is the calibrated retention time, and z, z+1 are the carbon numbers of n-alkane eluted before and after the pesticide compound (x) elution respectively, $t_R(z) < t_R(x) < t_R(z+1)$, generally the carbon number of n-alkane z is greater than 4.

13. The electronic ID database according to claim 2, wherein the chromatography mass spectrometry conditions are:

chromatography conditions: gas chromatographic column is TG-5SILMS, 30 m×0.25 mm (i.d.)×0.25 μm mass spectrometry special column; programmed temperature process: 40° C., kept for 1 minute; raised to 130° C. at 30° C./minute; raised to 250° C. at 5° C./minute; raised to 300° C. at 10° C./minute, and kept for 5 minutes; carrier gas: helium, purity >99.999%; flow rate: 1.2 mL/minute; injection port type: PTV; injection volume: 1 μL; and injection mode:

temperature programmed injection, splitless time 1.5 minutes; and mass spectrometry conditions: EI source voltage: 70 eV; ion source temperature: 230° C.;

transmission line temperature: 280° C.; solvent delay: 4 minutes; scan mode: Full MS; mass scan range: 50-600 m/z; resolution: 60,000 FHWM (200 m/z); and heptachlor epoxide is used to adjust retention time.

* * * * *